United States Patent
Mihashi et al.

(10) Patent No.: US 7,806,529 B2
(45) Date of Patent: Oct. 5, 2010

(54) DEVICE AND METHOD FOR OPTOMETRY

(75) Inventors: Toshifumi Mihashi, Tokyo (JP); Yoko Hirohara, Tokyo (JP); Mariko Kobayashi, Tokyo (JP)

(73) Assignee: Topcon Corporation, Tokyo (JP)

( * ) Notice: Subject to any disclaimer, the term of this patent is extended or adjusted under 35 U.S.C. 154(b) by 188 days.

(21) Appl. No.: 12/056,617

(22) Filed: Mar. 27, 2008

(65) Prior Publication Data

US 2008/0246921 A1    Oct. 9, 2008

(30) Foreign Application Priority Data

Mar. 30, 2007    (JP) .............. 2007-095058

(51) Int. Cl.
*A61B 3/02* (2006.01)
*A61B 3/10* (2006.01)

(52) U.S. Cl. ............... 351/240; 351/205; 351/233; 351/239

(58) Field of Classification Search ......... 351/233, 351/237, 239, 240
See application file for complete search history.

(56) References Cited

U.S. PATENT DOCUMENTS

| 5,483,305 | A | * | 1/1996 | Kohayakawa | ............ 351/243 |
| 6,802,609 | B2 | | 10/2004 | Mihashi et al. | |
| 2004/0095556 | A1 | | 5/2004 | Mihashi et al. | |
| 2005/0012896 | A1 | * | 1/2005 | Fukuma et al. | ............ 351/201 |
| 2005/0018132 | A1 | * | 1/2005 | Fukuma et al. | ............ 351/200 |
| 2005/0052715 | A1 | * | 3/2005 | Avudainayagam et al. | ..... 359/3 |
| 2006/0192920 | A1 | * | 8/2006 | Fujieda et al. | ............ 351/214 |

FOREIGN PATENT DOCUMENTS

| JP | 2001-321340 A | 11/2001 |
| JP | 2003-199712 A | 7/2003 |

* cited by examiner

*Primary Examiner*—Jordan M. Schwartz
(74) *Attorney, Agent, or Firm*—Foley & Lardner LLP

(57) ABSTRACT

An eye examination apparatus 100 of the present invention comprises, a refractive power measuring section 50 for measuring refractive powers of subject eyes E of a subject in a binocular viewing state, an eye chart presenting section 30 for presenting a subjective measurement eye chart to be observed by the subject, a correcting section 40 for correcting the subject eyes by referring to data on the refractive powers measured with the refractive power measuring section 50 and using the subjective measurement eye chart presented in the eye chart presenting section 30 and an optical characteristics measuring section 10 for subjectively measuring an optical characteristic of the subject eyes E corrected or being corrected with the correcting section 40 in a state where the subject is binocularly viewing the subjective measurement eye chart.

6 Claims, 20 Drawing Sheets

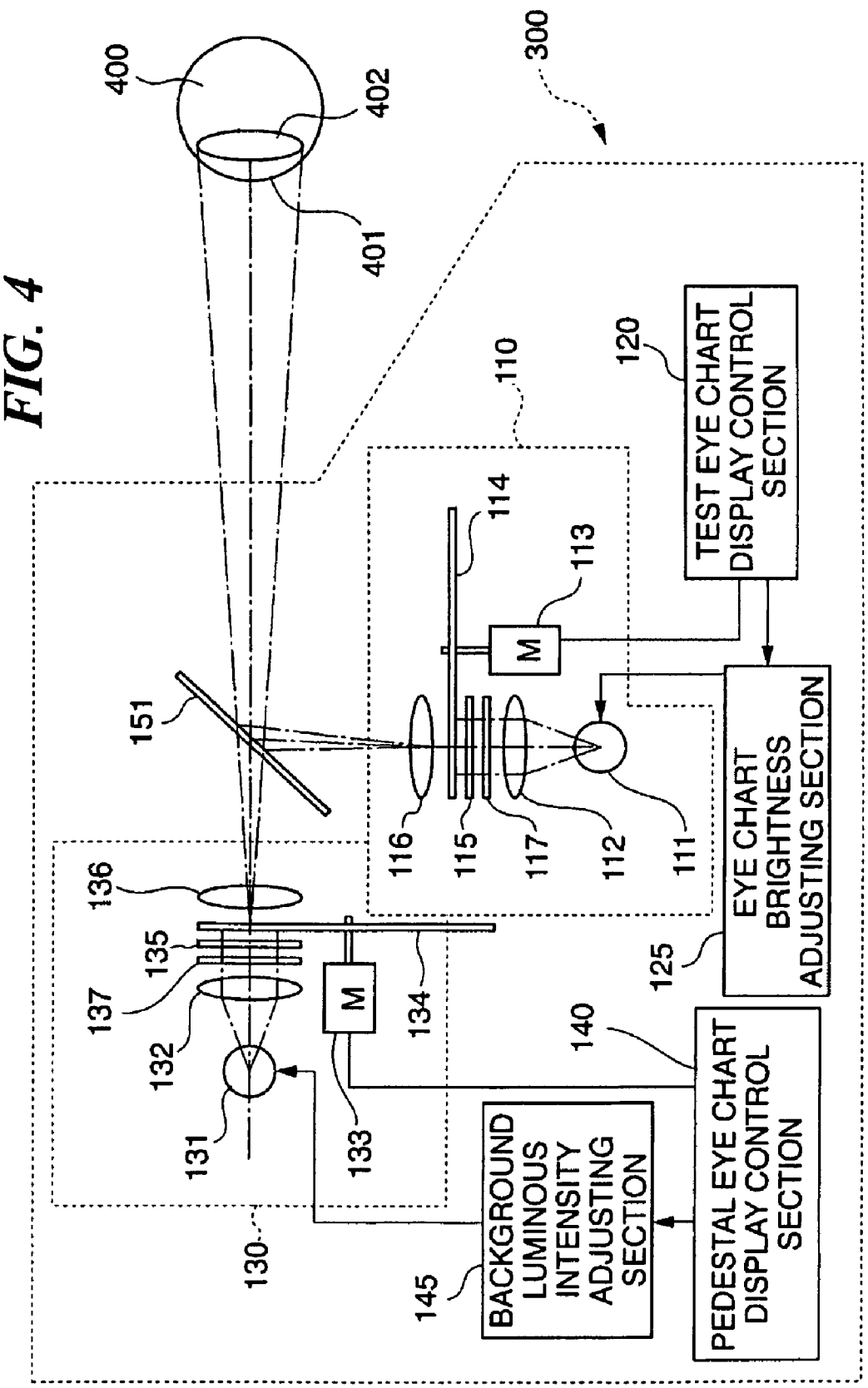

1300

1300

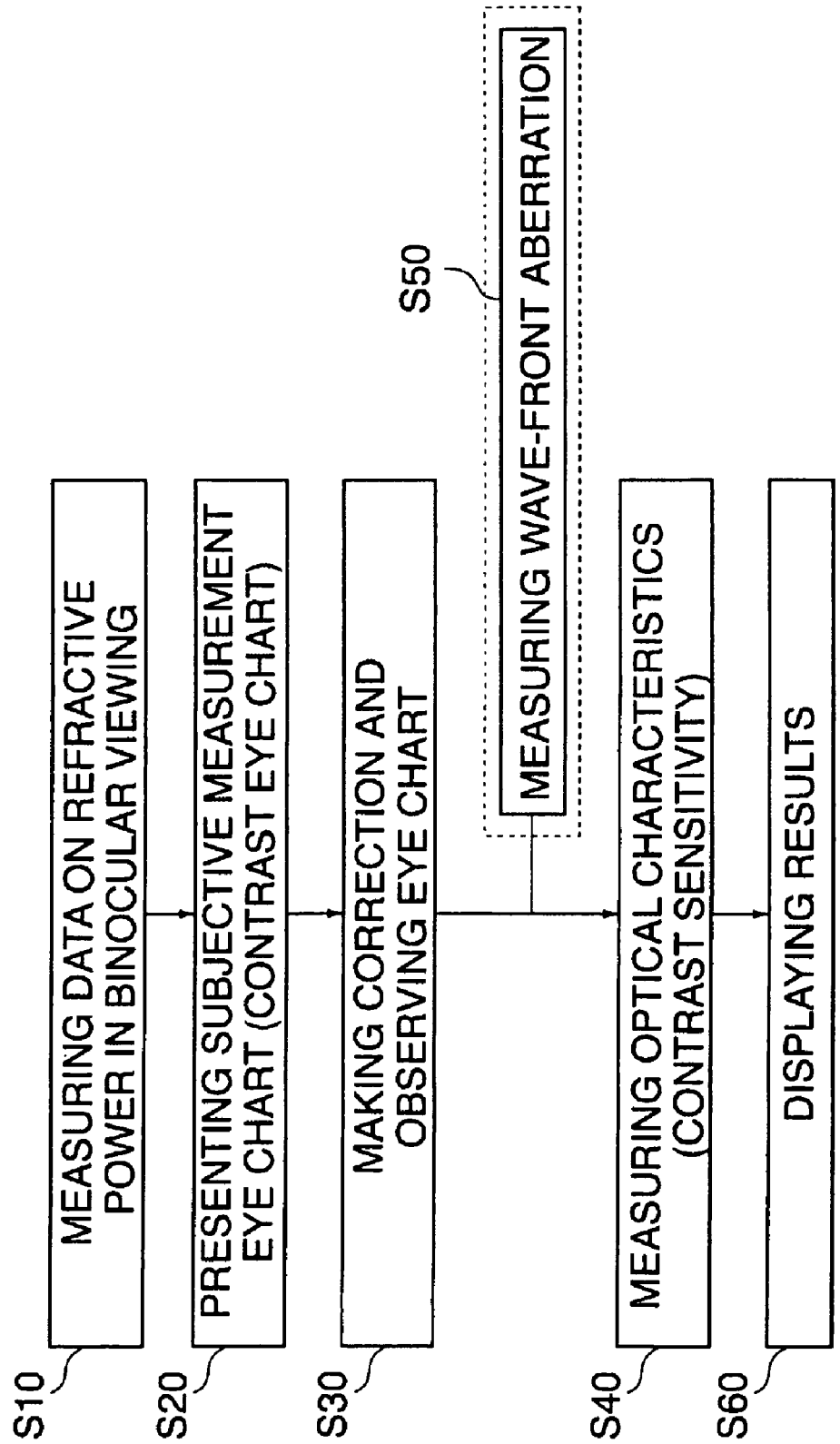

RIGHT EYE: 0.03

LEFT EYE: 0.01

BOTH EYES: 0.009

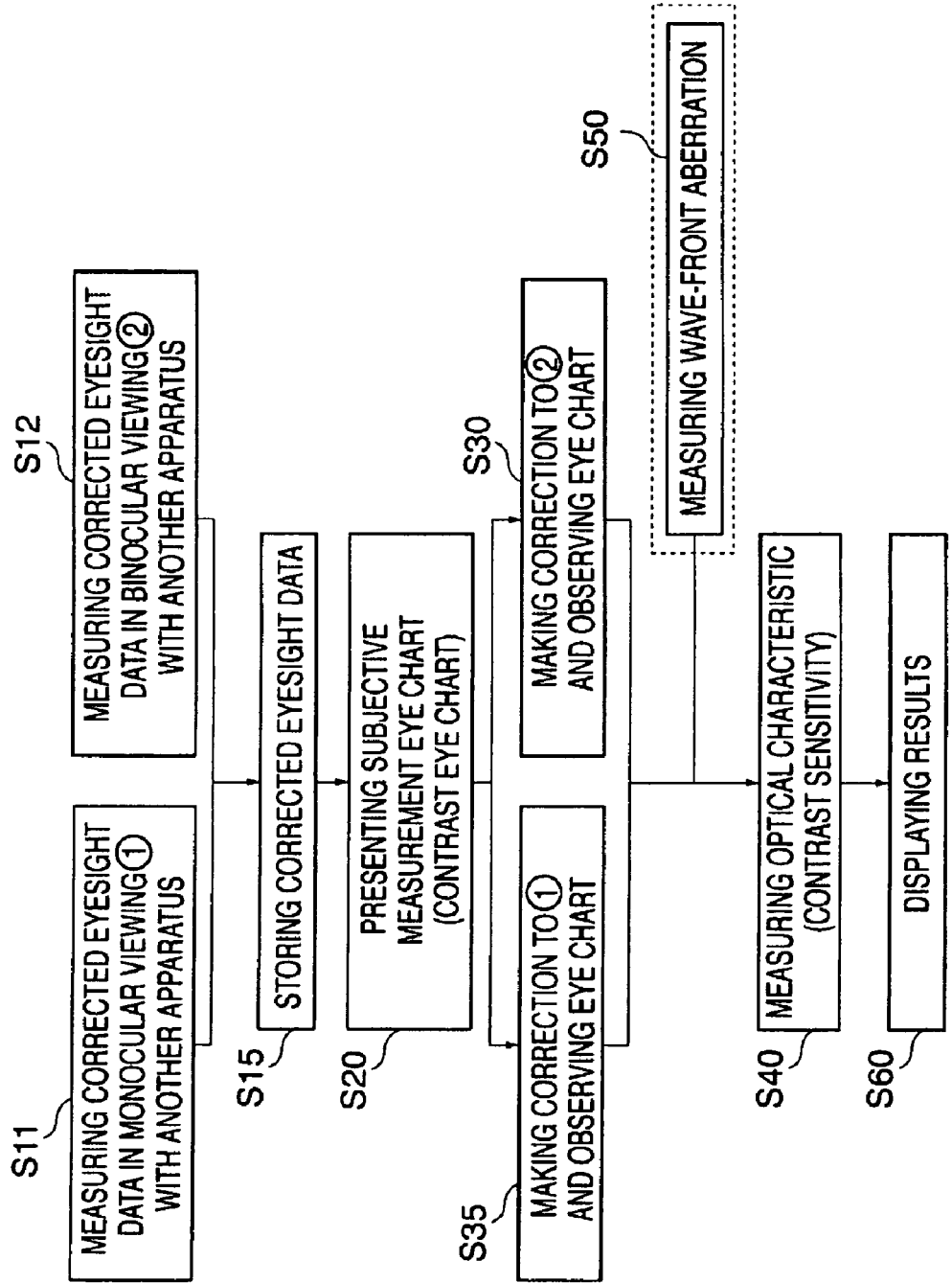

DEVICE AND METHOD FOR OPTOMETRY

BACKGROUND OF THE INVENTION

1. Technical Field

This invention relates to an eye examination apparatus (device for optometry) and an eye examination method (method for optometry). In particular, this invention relates to such apparatus and method for examining eyes that make it possible to measure optical characteristics when eyesight or contrast sensitivity is measured in the binocular viewing state.

2. Related Art

In measuring eyesight or contrast sensitivity using an eye chart for subjective measurement, the eyes are generally examined one by one. As it has been considered desirable to examine a single eye in a perfectly corrected state, the optical characteristics such as eyesight and contrast sensitivity have been actually measured with the eyesight corrected accordingly. In this regard, the inventors have disclosed an apparatus capable of measuring the contrast sensitivity of a subject eye accurately within a short time by measuring pupil area data on a subject; and an apparatus capable of measuring the optical characteristics with high accuracy by measuring reference light path. (Refer to Patent Documents 1 and 2.)

[Patent Document 1]
JP-A-2003-199712 (paragraphs 0020-0048, FIGS. 1-10)
[Patent Document 2]
JP-A-2001-321340 (paragraphs 0032-0160, FIGS. 1-10)

In measuring eyesight or contrast sensitivity using an eye chart for subjective measurement, it has been considered desirable to examine eyes in a perfectly corrected state and so measurements have been made for one eye at a time. Actually, however, as an object is observed using both eyes, there can be difference in the extent of correction between both eyes in the binocular viewing state.

In this case, there is a possibility of obtaining appropriate eyesight or contrast sensitivity in binocular viewing by making measurements in the binocular viewing state rather than making measurements with both eyes perfectly corrected. The optical characteristics data in such an appropriate binocular viewing state are also important.

An object of this invention is to provide an eye examination apparatus and an eye examination method that make it possible to measure eyesight or contrast sensitivity in the binocular viewing state and further make it possible to measure optical characteristics in such an appropriate binocular viewing state.

SUMMARY OF THE INVENTION

To solve the above mentioned problem, an eye examination apparatus 100 of Aspect (1) of the present invention, as shown in FIG. 1 for example, comprises: a refractive power measuring section 50 for measuring a refractive power of subject eyes E of a subject in a binocular viewing state; an eye chart presenting section 30 for presenting a subjective measurement eye chart to be observed by the subject; a correcting section 40 for correcting the subject eyes E by referring to data on the refractive power measured with the refractive power measuring section 50 and using the subjective measurement eye chart presented in the eye chart presenting section 30; and an optical characteristic measuring section 10 for measuring optical characteristics of the subject eyes E corrected or being corrected with the correcting section 40 in a state where the subject is binocularly viewing the subjective measurement eye chart.

Here, the refractive power measuring section, if it can utilize the function of the optical characteristic measuring section, need not necessarily be independent but may be a component in the optical characteristic measuring section. The "optical characteristics" is a generic term for characteristics including resolution characteristic, focal length, absorption, dispersion, refraction, polarization, light separation, frequency (color), etc., in addition to refractive power, high-order wave-front aberration, and contrast sensitivity. Here, the term should include at least refractive power, high-order wave-front aberration, and contrast sensitivity. The above constitution makes it possible to provide an eye examination apparatus capable of measuring the eyesight or contrast sensitivity in the binocular viewing state and further capable of measuring the optical characteristics in such an appropriate binocular viewing state.

The invention of Aspect (2) of the present invention is the eye examination apparatus of Aspect (1), wherein the subjective measurement eye chart is an eye chart for subjectively measuring eyesight and the optical characteristic measuring section 10 is constituted to measure the subjective eyesight of the subject.

The above constitution makes it possible to measure eyesight subjectively in the binocular viewing state.

The invention of Aspect (3) of the present invention is the eye examination apparatus 100 of Aspect (1), wherein, as shown in FIG. 1 for example, the subjective measurement eye chart is an eye chart for subjectively measuring contrast sensitivity, and the optical characteristic measuring section 10 is constituted to subjectively measure the contrast sensitivity of the subject.

The above constitution makes it possible to measure contrast sensitivity subjectively in the binocular viewing state.

The invention of Aspect (4) of the present invention is the eye examination apparatus 100 of Aspect (2) or (3), as shown in FIG. 1 for example, comprises a wave-front aberration measuring section 20 for measuring the wave-front aberration of the subject eyes E in the state where the subject is binocularly viewing the subjective measurement eye chart, based on a light reception signal occurring when a light receiving element 1310 (refer to FIG. 7) receives light which is cast as measurement-use light so as to converge at a point on a fundus of the subject eye E and is reflected from the fundus of the subject eye.

Here, the wave-front aberration measuring section, if it can utilize the function of the optical characteristic measuring section, need not necessarily be independent but may be a component in the optical characteristic measuring section. The above constitution makes it possible to measure the wave-front aberration in the binocular viewing state.

The invention of Aspect (5) of the present invention is the eye examination apparatus of Aspect (4), wherein the wave-front aberration measuring section 20 has: a first mode in which measurement-use light is cast to enter both the subject eyes E at the same time so as to converge at a point on the fundi, and the lights reflected from the subject eyes E are received to measure the wave-front aberration of the subject eyes E; and a second mode in which, in order to objectively measure the refractive power, measurement-use light is cast to enter the subject eyes E one by one so as to converge at a point on the fundus, and the light reflected from the subject eye E is received to measure the wave-front aberration of the subject eye E.

The above constitution makes it possible to measure the wave-front aberration in both binocular and monocular viewing, and it is possible to compare both kinds of data.

An eye examination apparatus 100A of Aspect (6) comprises: as shown in FIG. 16 for example, a storage section 45 for storing refractive power data on subject eyes E of a subject in a binocular viewing state; an eye chart presenting section 30 for presenting a subjective measurement eye chart to be observed by the subject; a correcting section 40 for correcting the subject eyes E by referring to the refractive power data stored in the storage section 45 and using the subjective measurement eye chart presented in the eye chart presenting section 30; and an optical characteristic measuring section 10 for measuring optical characteristics of the subject eyes E corrected or being corrected with the correcting section 40 in a state where the subject is binocularly viewing the subjective measurement eye chart.

The above constitution makes the apparatus simple in constitution by utilizing refractive power data obtained with the other apparatuses.

To solve the above mentioned problem, an eye examination method of Aspect (7) of the present invention comprises: as shown in FIG. 11 for example, a refractive power measuring step S10 of measuring a refractive power of subject eyes E of a subject in a binocular viewing state; an eye chart presenting step S20 of presenting a subjective measurement eye chart to be observed by the subject; a correcting step S30 of correcting the subject eyes by referring to data of the refractive power measured in the refractive power measuring step S10 and using the subjective measurement eye chart presented in the eye chart presenting step S20; and an optical characteristic measuring step S40 of measuring optical characteristics of the subject eyes E corrected or being corrected in the correcting step S30 in a state where the subject is binocularly viewing the subjective measurement eye chart.

The above constitution can provide an eye examination method that makes it possible to measure eyesight or contrast sensitivity in the binocular viewing state and further to measure optical characteristics in such an appropriate binocular viewing state.

The invention of Aspect (8) of the present invention is the eye examination method of Aspect (7), wherein the subject eyes are corrected in the correcting step S30 such that when contrast sensitivity or eyesight is measured, a dominant eye is corrected perfectly and the other eye is corrected so as to be adjusted in the binocular viewing state.

The above constitution makes it possible to make correction efficient.

According to this invention, it is possible to provide an eye examination apparatus and an eye examination method that make it possible to measure eyesight or contrast sensitivity in the binocular viewing state and further make it possible to measure optical characteristics in such an appropriate binocular viewing state.

This application is based on the Patent Application No. 2007-095058 filed on Mar. 30, 2007 in Japan, the contents of which are hereby incorporated in its entirety by reference into the present application, as part thereof.

The present invention will become more fully understood from the detailed description given hereinbelow. However, the detailed description and the specific embodiment are illustrated of desired embodiments of the present invention and are described only for the purpose of explanation. Various changes and modifications will be apparent to those ordinary skilled in the art on the basis of the detailed description.

The applicant has no intention to give to public any disclosed embodiment. Among the disclosed changes and modifications, those which may not literally fall within the scope of the patent claims constitute, therefore, a part of the present invention in the sense of doctrine of equivalents.

The use of the terms "a" and "an" and "the" and similar referents in the context of describing the invention (especially in the context of the following claims) are to be construed to cover both the singular and the plural, unless otherwise indicated herein or clearly contradicted by context. The use of any and all examples, or exemplary language (e.g., "such as") provided herein, is intended merely to better illuminate the invention and does not pose a limitation on the scope of the invention unless otherwise claimed.

BRIEF DESCRIPTION OF THE DRAWINGS

FIG. 4 shows a constitution example of a contrast eye chart presenting system.

FIG. 11 shows an example of process flow of the eye examination method as the first embodiment of this invention.

FIG. 19 shows a process flow example of the eye examination method as a sixth embodiment of this invention.

DETAILED DESCRIPTION OF THE PREFERRED EMBODIMENTS

Embodiments of this invention will be described below in reference to appended drawings.

First Embodiment

Figure 1:
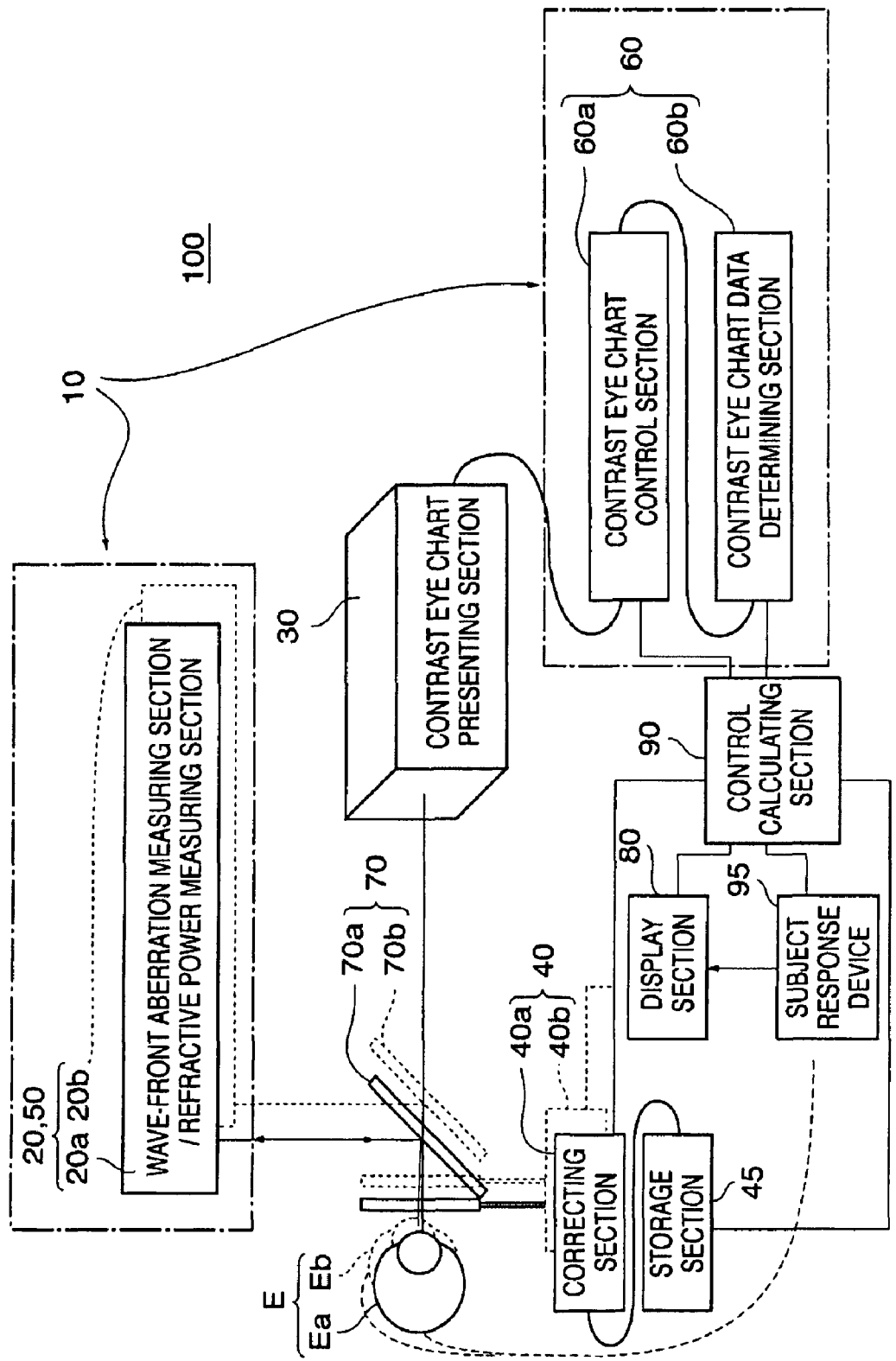
FIG. 1 shows a constitution example of an eye examination apparatus as a first embodiment of this invention.

FIG. 1 shows a constitution example of an eye examination apparatus as a first embodiment of this invention. With the constitution of this embodiment, it is possible to measure wave-front aberration in addition to optical characteristics, and an optical characteristic section is utilized to measure refractive power. It is also constituted to make subjective measurements by presenting a contrast eye chart to a subject.

In FIG. 1, E denotes a subject eye. An eye examination apparatus 100 includes: a wave-front aberration measuring section 20 for measuring wave-front aberration as an optical characteristic of the subject eye E, an eye chart presenting section 30 for presenting an eye chart to the subject eye E (here, it functions as a contrast eye chart presenting section for presenting a contrast eye chart), a correcting section 40 for correcting the subject eye E by making it possible to choose an appropriate lens while changing various lenses placed in front of the subject eye E, a storage section 45 for storing correction data, etc., a refractive power measuring section 50 for measuring the refractive power of the subject eye E for correcting or measuring optical characteristics, a contrast sensitivity specifying section 60 for determining the eye chart to be presented to the subject eye E and causing the eye chart presenting section 30 to present it (here, it is composed of a contrast eye chart data determining section 60b for determining a contrast eye chart, and a contrast eye chart control section 60a for controlling the contrast eye chart presenting section 30 to cause it to present the contrast eye chart determined with the contrast eye chart data determining section 60b), a dichroic mirror 70 for reflecting light reflected from the subject eye E toward both the wave-front aberration measuring section 20 and the refractive power measuring section 50 while transmitting visible light from the contrast eye chart presenting section 30, a display section 80 for displaying measurement results and analysis results for the subject eye E, and a control calculating section 90 for controlling the above sections so that they carry out various measurements for the subject eye E. Here, the refractive power measuring section 50 may utilize the function of the optical characteristic measuring section 10 and is provided in the optical characteristic measuring section 10. Sections that may function as the optical characteristic measuring section 10 are: the wave-front aberration measuring section 20, the refractive power measuring section 50, and the contrast sensitivity specifying section 60. The contrast sensitivity of the subject eye E is obtained from the subject's subjective response data when the subject eye E is caused to observe the contrast eye chart through a lens in the correcting section 40. Further, supporting data at that time are obtained by measuring optical characteristics such as the high-order wave-front aberration of the subject eye E using the optical characteristic measuring section 10.

Here, in order to make measurements in the binocular viewing state in this embodiment, the wave-front aberration measuring sections 20, the refractive power measuring sections 50, the correcting sections 40, and the dichroic mirrors 70 are provided in pairs corresponding to both the right and left eyes E, with letters a and b suffixed to the reference numerals representing right and left. The eye chart presenting section 30, the contrast sensitivity specifying section 60, the display section 80, and the control calculating section 90 are provided one for each. The dichroic mirror 70 reflects near infrared rays while transmitting visible light.

Figure 2:
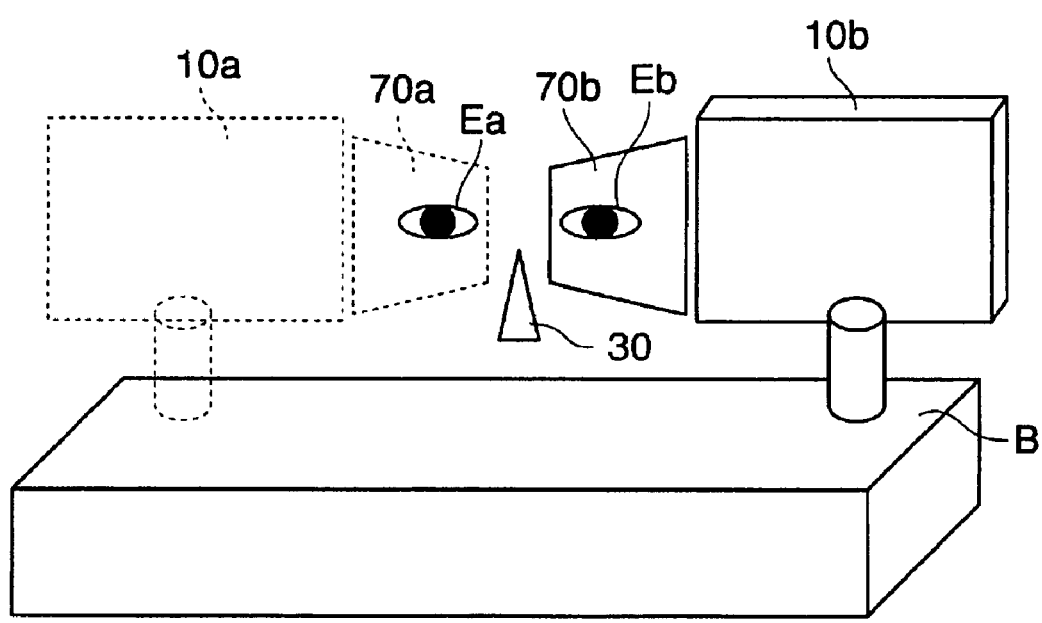
FIG. 2 is a schematic view of the layout of an optical characteristic measuring section.

FIG. 2 schematically shows the layout of the optical characteristic measuring section 10. As shown in FIG. 2, the right and left subject eyes Ea and Eb observe through right and left dichroic mirrors 70a and 70b an eye chart presented in the contrast eye chart presenting section 30. Light beams from the optical characteristic measuring section 10 travel toward the right and left subject eyes Ea and Eb, are reflected at the fundi of the right and left subject eyes Ea and Eb, are reflected again with the right and left dichroic mirrors 70a and 70b, enter right and left optical characteristic measuring sections 10a and 10b, and are measured. These optical components, excluding the subject eyes Ea and Eb, are placed together on a single stage B. The "optical characteristics" is a generic term for characteristics including resolution characteristic, focal length, absorption, dispersion, refraction, polarization, light separation, frequency (color), etc., in addition to refractive power, high-order wave-front aberration, and contrast sensitivity. Here, the term includes at least refractive power, high-order wave-front aberration, and contrast sensitivity.

Figure 3:
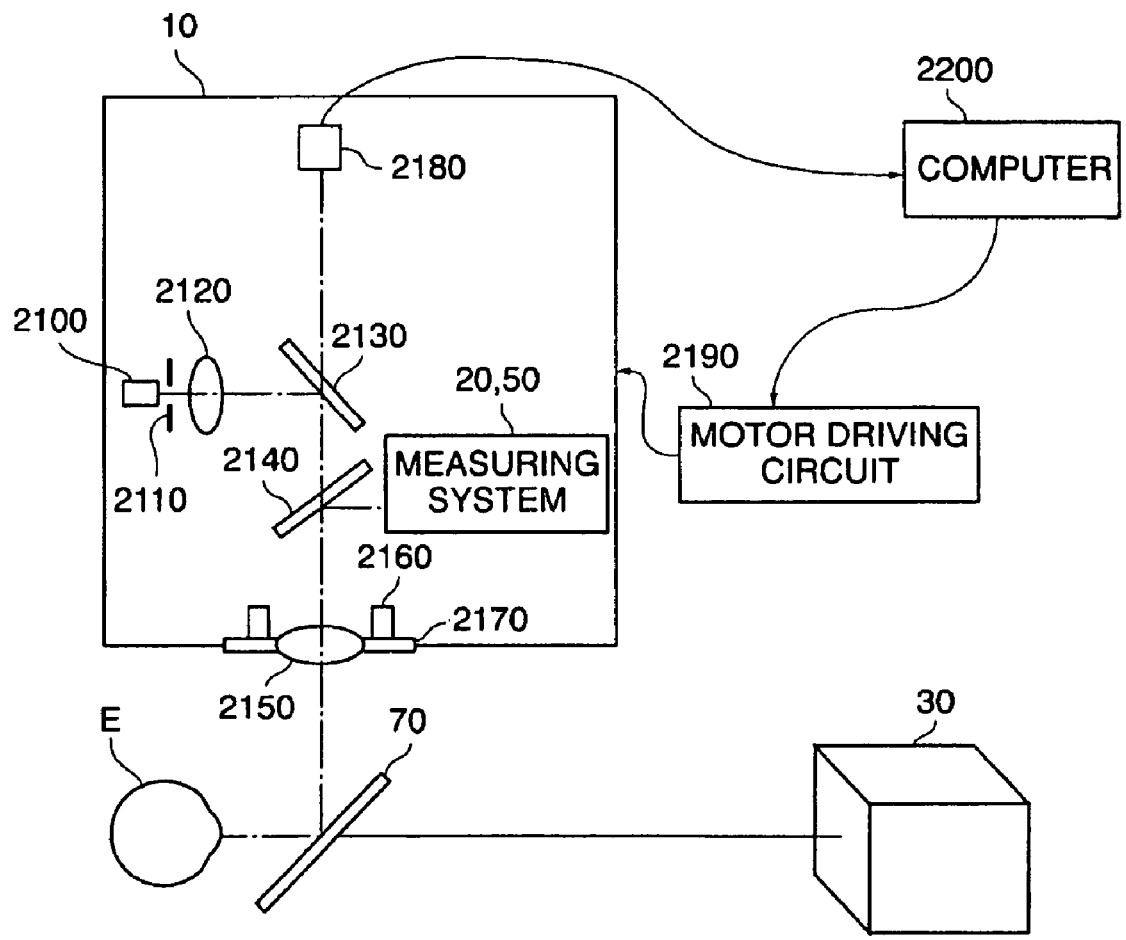
FIG. 3 shows an optical layout example of the optical characteristic measuring section.

FIG. 3 shows an optical layout example of the optical characteristic measuring section 10. The dichroic mirror 70 has a property of reflecting near infrared rays while permitting visible light to pass through. Therefore, the subject can observe visible light coming from the contrast eye chart presenting section 30 through the dichroic mirror 70. As near infrared rays are reflected with the dichroic mirror 70, the near infrared rays ($\lambda 1$, $\lambda 2$) from the optical characteristic measuring section 10 are reflected with the dichroic mirror 70, and enter the subject eye E. The near infrared rays from the subject eye E are reflected again with the dichroic mirror 70, and travel toward the optical characteristic measuring section 10. The optical characteristic measuring section 10 has functions, in addition to the function of measuring the optical characteristics, of X-Y position adjustment or position matching in the direction perpendicular to the optical axis, and working distance adjustment or position matching of the subject eye E and the optical characteristic measuring system in the direction of the optical axis.

The X-Y position adjustment or position matching in the direction perpendicular to the optical axis is carried out with the following setup. The light from a light source 2100 of a wavelength $\lambda 1$ is made into a parallel beam through a pinhole 2110 and a condenser lens 2120, reflected with a half-reflecting mirror 2130, passes through a dichroic mirror 2140, passes through a condenser lens 2150, is reflected with the dichroic mirror 70, and made to converge at a position half from the center of the corneal curvature of the subject eye E to the corneal vertex of the subject eye E to form a bright spot at the peak of the cornea of the subject eye. While observing it with an observation-use CCD 2180, X-Y position adjustment is carried out by adjusting such that the bright spot formed at the peak of the cornea of the subject eye is located on the optical axis.

Next, the working distance adjustment or position matching of the subject eye E and the optical characteristic measuring system in the direction of the optical axis is carried out with the following setup. Two, right and left spotlight sources 2160 each emitting a thin parallel light beam of a wavelength $\lambda 1$, and a ring-shaped illumination 2170 emitting diffused rays, are disposed around the condenser lens 2150, and respective images are formed by reflection with the cornea of the subject eye. Here, the distance between the two small spot images formed with the light beams from the right and left spotlight sources 2160 is constant irrespective of the distance between the subject eye E and the optical characteristic measuring system. On the other hand, the size of the ring-shaped image formed with the light beam from the ring-shaped illumination 2170 emitting diffused rays varies with the distance between the subject eye E and the optical characteristic measuring system. Therefore, on the basis of the distance, as a reference distance, between the two spot images formed with the light beams from the spotlight sources 2160 invariable with the working distance, the working distance adjustment is made such that the size of the ring-shaped image formed with the light beam from the ring-shaped illumination 2170 varying in size with the working distance satisfies a specified relationship.

The light beam of a wavelength λ2 from the measuring system including the refractive power measuring sections 50 and the wave-front aberration measuring section 20 is reflected with the dichroic mirror 2140 and travels toward the subject eye E. The light beam of a wavelength λ2 reflected from the subject eye E is reflected with the dichroic mirror 2140 and enters the measuring systems 20 and 50. The light of a wavelength λ1 (>λ2) passes through both the dichroic mirror 2140 and the half-reflecting mirror 2130, and is received with the observation-use CCD 2180.

While the screen of the observation-use CCD 2180 is being observed, the distance between the optical characteristic measuring section 10 and the subject eye E or their positional relationship is made adjustable by the control of a computer 2200. These optical systems may also be driven to rotate about the optical axis with a motor 2190 as controlled with the computer 2200 to change the direction of observation.

FIG. 4 shows a constitution example of a contrast eye chart presenting system 300. The optical system and the control system are shown in the same drawing. While two subject eyes E (400) and light separation mirrors 151 are present respectively, only one of them are respectively shown in the drawing for simplicity. In the drawing, the contrast eye chart measuring system includes: a first illumination optical system 110, a test eye chart display control section 120, a second illumination optical system 130, and a pedestal eye chart display control section 140. The contrast eye chart control section 60a has the test eye chart display control section 120 and the pedestal eye chart display control section 140.

The first illumination optical system 110 is mainly to form test eye charts such as a contrast eye chart, and includes: a light source 111, a condenser lens 112, a rotary motor 113 for replacing eye charts, an eye chart plate 114, an ND (neutral density) filter 115, a magnification correcting lens 116, and a diffusion plate 117. The condenser lens 112 makes the light radiated from the light source 111 into a parallel light beam. On the eye chart plate 114 is printed, as a contrast eye chart, an eye chart for testing contrast sensitivity such as Gabor stimulus suited for measuring space frequency characteristic. On the contrast eye chart is drawn a pattern of stripes that produces space frequencies of for example 1.5, 3, 6, 12, and 18 (cycles/deg) at a viewing distance of 3 meters.

The ND filter 115 is a filter that changes only the light amount with a transmission rate of such as 60% and 40%; it does not cause polarization or other effects. The magnification correcting lens 116 has a focal length of infinity (0 diopter), meters (0.2 diopters), etc. Magnification is changed by replacing the magnification correcting lens 116 before an eye chart is presented to the subject. The diffusion plate 117 diffuses light coming through the condenser lens 112 to equalize the light amount distribution.

The eye chart display control section 120 controls the drive of the rotary motor 113 for replacing eye charts such that the eye chart plate 114 is stopped at an appropriate position and an appropriate eye chart is presented to the subject. The eye chart display control section 120 also functions as an eye chart brightness control means that sends a brightness control signal to an eye chart brightness adjusting section 125. The section 120 receives the value of the diameter of the subject's pupil area (pupil diameter value) measured with the optical characteristic measuring section 10 and outputs a control signal for controlling the brightness of the contrast eye chart such that the pupil diameter satisfies a specified value. The eye chart brightness adjusting section 125 is to adjust the brightness of the contrast eye chart. For example, the section 125 adjusts electric power to adjust the light amount of the light source 111, replaces the ND filter 115 for adjusting the amount of transmission light, etc.

The second illumination optical system 130 is mainly to form a background such as a pedestal eye chart, and includes: a light source 131, a condenser lens 132, a rotary motor 133 for replacing eye charts, an eye chart plate 134, an ND filter 135, a magnification correcting lens 136, and a diffusion plate 137. The second illumination optical system 130, while including roughly the same optical components as those of the first illumination optical system 110, is different in that the eye chart printed on the eye chart plate 134 is a background. As for the contrast eye chart, because a test eye chart having a specified space frequency and a specified contrast is printed, the printing is made such that background brightness may be adjusted to result in roughly the same brightness with different eye charts. Here, the contrast is given as the difference in transmission factor between the pedestal eye chart and the test eye chart. Further it is possible for the pedestal eye chart to use, in place of 100% transmission, for example a white noise or filtered band restriction noise stimulus.

The pedestal eye chart display control section 140 controls the drive of the rotary motor 133 for replacing eye charts to stop the eye chart plate 134 at an appropriate position so that a pedestal eye chart having contrast or brightness corresponding to the test eye chart is presented to the subject. The pedestal eye chart display control section 140 also functions as a background illumination control means that receives the pupil diameter value of the subject eye E measured with the optical characteristic measuring section 10, and sends a background illumination control signal to a background illumination adjusting section 145 such that the pupil diameter satisfies a specified value. The background illumination adjusting section 145 is to adjust the background illumination of the contrast eye chart. For example, the section 145 adjusts electric power to adjust the light amount of the light source 131, replaces the ND filter 135 for adjusting the amount of transmission light, etc.

The test eye chart (contrast eye chart) sent from the first illumination optical system 110 and the pedestal eye chart (background illumination) sent from the second illumination optical system 130 are superimposed on the same light path using a mirror 151. The mirror 151 may be for example a half-reflecting mirror. Or, the ratio of transmission factor to reflection factor may be determined to match the light amount required for the light sources 111 and 131. Appropriately determining the ratio of transmission factor to reflection factor of the mirror 151 improves energy efficiency in comparison with the case in which light is constantly attenuated with the ND filters 115 and 135.

Referring to FIG. 1 again, the control calculating section 90 has also the function of a measurement timing forming section to produce timing signals according to which the contrast eye chart presenting section 30 presents a contrast eye chart to a front part 401 of the subject eye E (see FIG. 4). Further, the contrast eye chart control section 60a has also the function of combining together and processing the contrast and eyesight information presented by the contrast eye chart presenting section 30. A subject response device 95 is to input the response of the subject to the contrast eye chart. An input-output device such as a mouse is used as the subject response device 95. Output signals from the subject response device 95 are inputted through the control calculating section 90 into the contrast eye chart control section 60a.

Figure 5A:
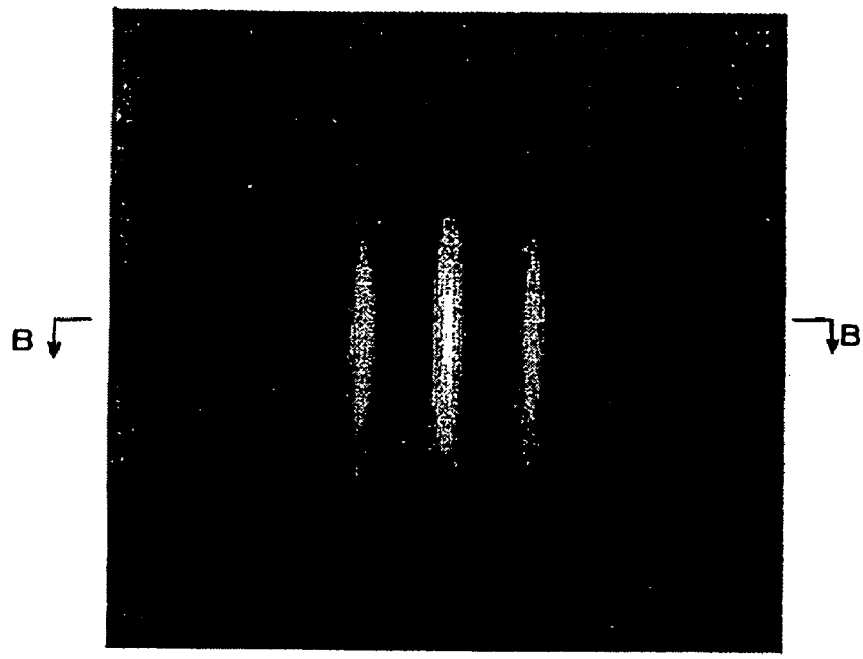
FIGS. 5A and 5B are an explanatory drawing of contrast using a contrast eye chart.
Figure 5B:
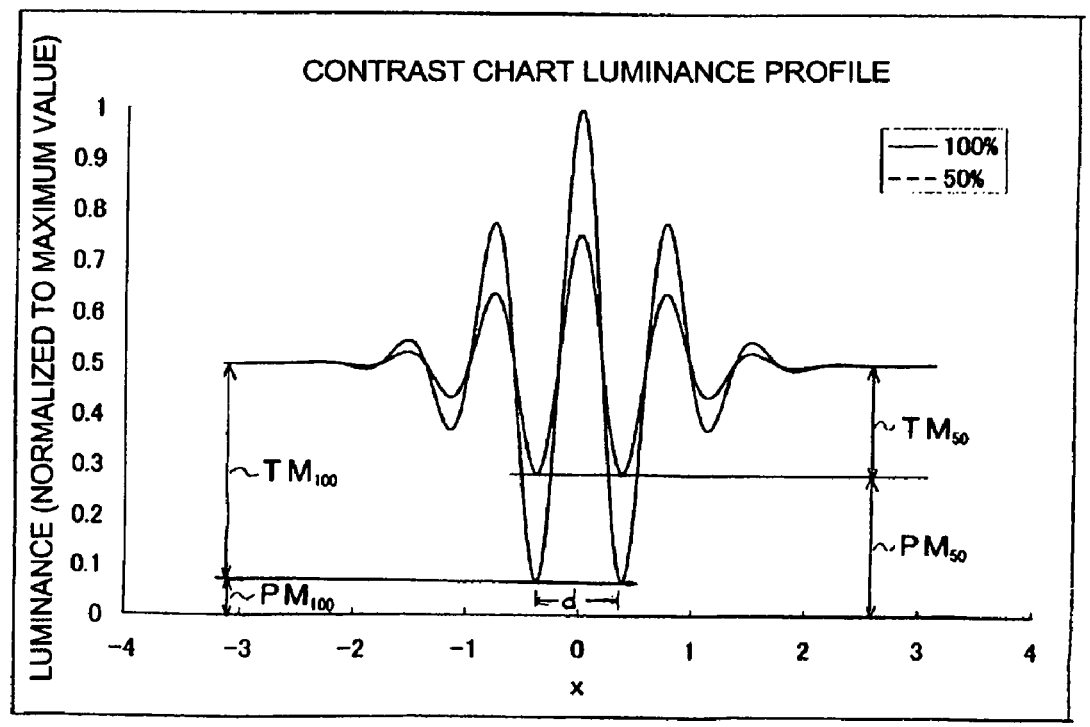

FIG. 5 is an explanatory drawing of contrast using a contrast eye chart, in which FIG. 5A is a plan view of a Gabor stimulus projected on the front part of the subject eye E, and FIG. 5B shows a contrast chart luminance profile as seen along the line B-B in the plan view of FIG. 5A. The horizontal axis x represents the position on the chart. The peak to peak interval d of the luminance profile corresponds to the space frequency. When the contrast is 100%, because the luminance amplitude of the test eye chart $TM_{100}$ using the Gabor stimulus is great, the luminance of the pedestal eye chart $TM_{100}$ is about 0.08, the minimum value of the Gabor stimulus. On the other hand, when the contrast is 50%, because the luminance amplitude of the test eye chart $TM_{50}$ using the Gabor stimulus is smaller than the test eye chart $TM_{100}$, the luminance of the pedestal eye chart $PM_{50}$ is about 0.28, the minimum value of the Gabor stimulus.

In other words, as the luminance amplitude of the test eye chart varies according to the contrast in the plan view of the Gabor stimulus, it is necessary to choose the pedestal eye chart of a transmission factor corresponding to the luminance amplitude of the Gabor stimulus, so that the brightness of the contrast eye chart is equal. Therefore, the contrast eye chart control section 60a drives the rotary motors 113 and 133 for replacing eye charts to produce appropriate combination of the eye chart plates 114 and 134. Incidentally, it is also possible for the contrast eye chart control section 60a to appropriately adjust the light amount of the light sources 111 and 131 or the transmission factors of the ND filters 115 and 135, so that the brightness of the contrast eye chart is equal.

For presenting the contrast eye chart, for example an up-down method is used. The up-down method is a kind of psychological measuring method or a forced choice method in which stimulus is given for one time in one trial by presenting a contrast eye chart and a contrast-less eye chart side by side, and the subject is required to tell the position where the Gabor stimulus is located. To present the contrast eye chart for one time, first a background is presented to the subject, then a Gabor stimulus is presented, and the response of the subject is stored. Then, the contrast eye chart control section 60a presents the Gabor stimulus to the subject until the measurement is over.

Figure 6A:
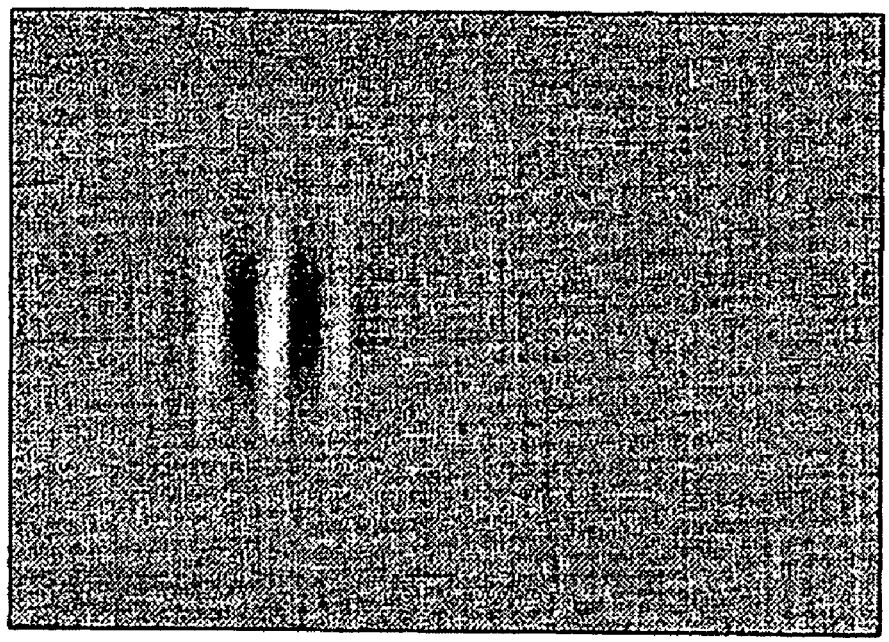
FIGS. 6A and 6B show examples of contrast eye chart presented in an up-down method.
Figure 6B:
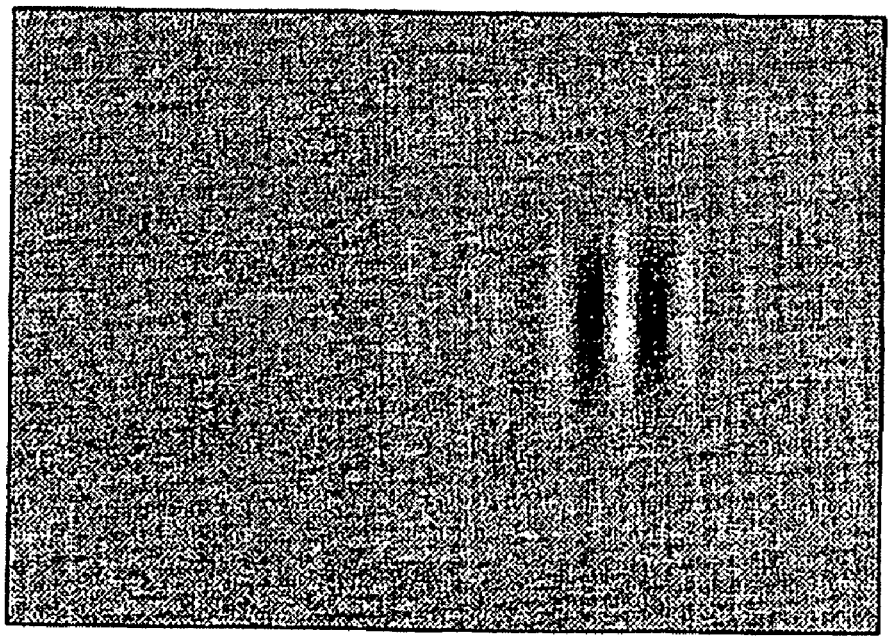

FIG. 6 shows examples of contrast eye chart presented in the up-down method. In FIG. 6A, an eye chart of high contrast is shown on the left hand; and a contrast-less eye chart, on the right hand. In FIG. 6B, an eye chart of high contrast is shown on the right hand; and a contrast-less eye chart, on the left hand. The subject is to respond to the eye chart presented. When the contrast eye chart is presented in the up-down method, as the stimulus is presented in the two alternative forced choice method (2AFC method), the subject is to respond by telling where the Gabor stimulus is located. The response of the subject may be given through a response device such as a mouse or by speech.

Figure 7:
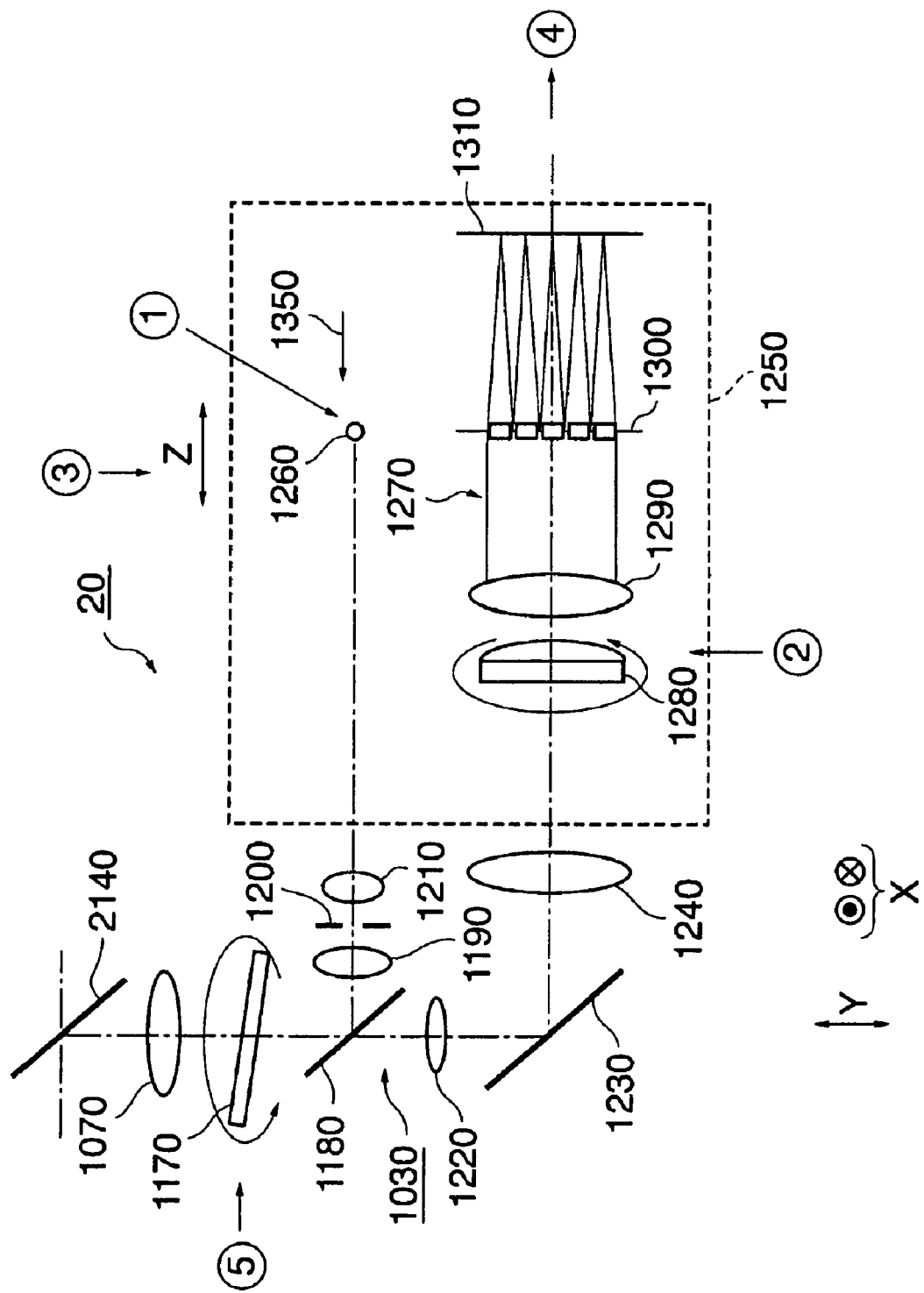
FIG. 7 shows a constitution example of a wave-front aberration measuring section.

FIG. 7 shows a constitution example of the wave-front aberration measuring section 20. To the wave-front aberration measuring section 20, light is separated with the dichroic mirror 2140 (see FIG. 3). The wave-front aberration measuring section 20 comprises a measuring optical system 1030 and a measuring unit 1250. The measuring optical system 1030 has: an objective lens 1070, a rotary prism 1170, a beam splitter 1180, a relay lens 1190, an iris aperture 1200, a relay lens 1210, a relay lens 1220, a half-reflecting mirror 1230, and a relay lens 1240. An optical system of a sight line direction detector (not shown here) is disposed behind the half-reflecting mirror 1230.

The measuring unit 1250 is roughly made up of a measurement light projecting source 1260 and a measurement light receiving optical system 1270. Together with the relay lens 1210, the iris aperture 1200, the relay lens 1190, the beam splitter 1180, the rotary prism 1170, the objective lens 1070, and the dichroic mirror 2140, the measurement light projecting source 1260 constitutes a light casting system for casting a light beam of a specified pattern to the subject eye E. The iris aperture 1200 is made conjugate with the pupil of the subject eye E. The measurement light projecting source 1260 is made conjugate with the fundus of the subject eye E. The rotary prism 1170 is kept rotating during the measurement.

The measurement light from the measurement light projecting source 1260 is cast to the fundus of the subject eye E through the relay lens 1210, the iris aperture 1200, the relay lens 1190, the beam splitter 1180, the rotary prism 1170, the objective lens 1070, and the dichroic mirror 2140.

The measuring unit 1250 has: a variable cross cylinder 1280, an image forming lens 1290, a Hartmann plate 1300, and a light receiving element 1310 as a light receiving section (for example a wave-front sensor). The image forming lens 1290 functions as a focusing optical member for adjusting the state of light beam so as to converge the light reflected from the subject eye E into focus.

Figure 8A:
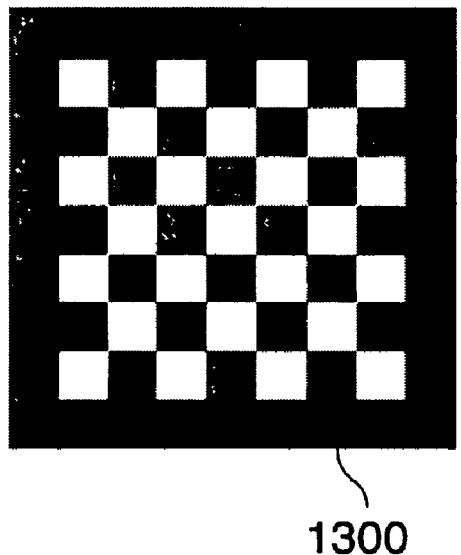
FIGS. 8A and 8B show examples of Hartmann plate.
Figure 8B:
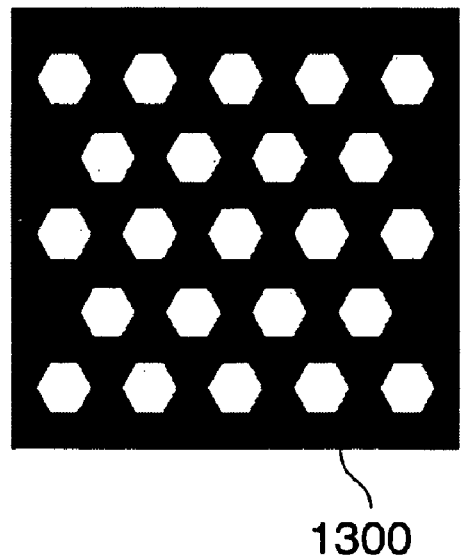

FIG. 8 shows examples of Hartmann plate. The Hartmann plate 1300 functions as a light splitting optical element for splitting the measurement light beam from the image forming lens 1290 into a plurality of light beams. Together with the half-reflecting mirror 2140, the objective lens 1070, the rotary prism 1170, the half-reflecting mirror 1180, the relay lens 1220, the reflecting mirror 1230, and the relay lens 1240, the variable cross cylinder 1280, the image forming lens 1290, the Hartmann plate 1300, and the light receiving element 1310 constitute a measurement light receiving optical system. The Hartmann plate 1300 is made up for example of minute lens plates at equal intervals. When a parallel light beam enters the Hartmann plate 1300, a lens array image 1320 at equal intervals is formed on the light receiving element 1310.

Figure 9:
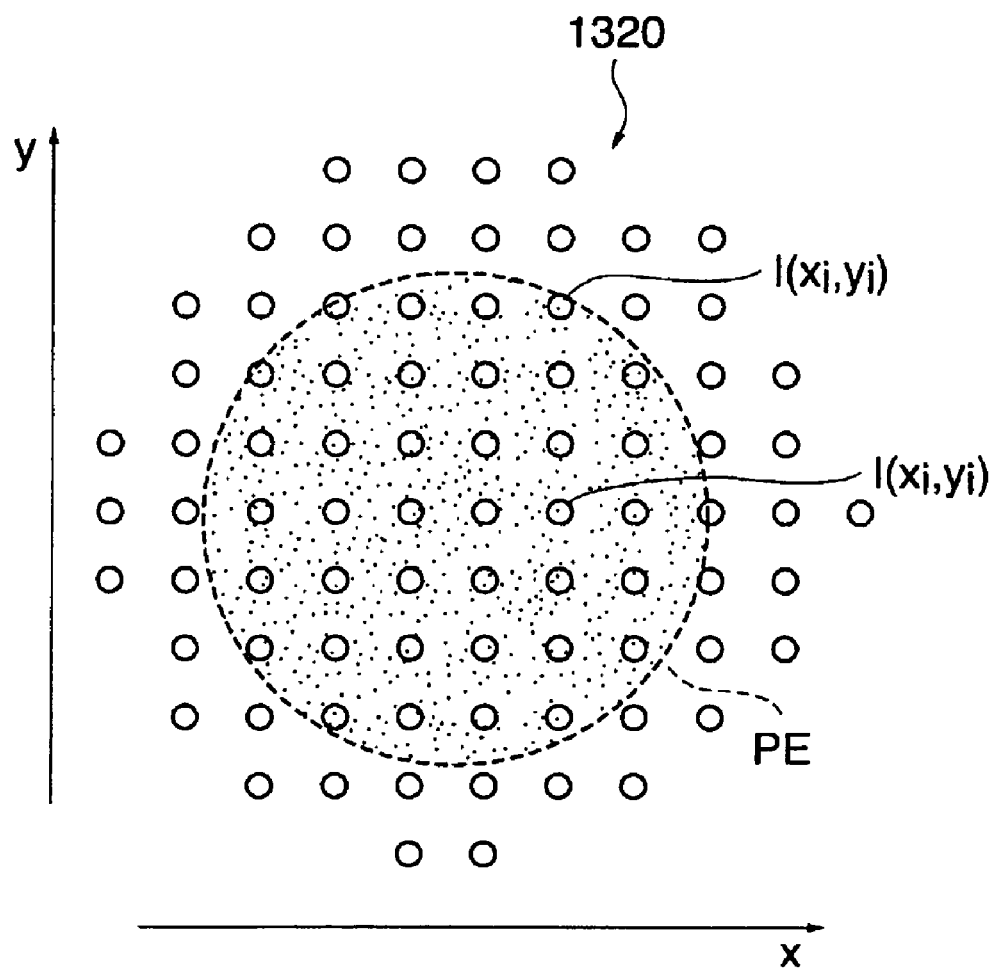
FIG. 9 shows a lens array image formed on a light receiving element using a Hartmann plate.

FIG. 9 shows an example of lens array image formed on the light receiving element 1310 using the Hartmann plate 1300. The intervals in the lens array image 1320 are the same as the intervals of the minute lens plates. Here, the horizontal axis X corresponds for example to the lateral (right and left) direction of the subject eye E; and the vertical axis Y, the vertical direction of the subject eye E. I (xi, yi) is the light amount intensity of the lens array image 1320 at the point (xi, yi). Incidentally, when a measurement light beam from the subject eye E enters the Hartmann plate 1300 in a myopic relationship, the image intervals in the lens array image 1320 become smaller than the lattice intervals of the minute lens plate; and when a measurement light beam from the subject eye E enters the Hartmann plate 1300 in a hyperopic relationship, the image intervals in the lens array image 1320 become greater than the lattice intervals of the minute lens plate. Incidentally, a micro Fresnel lens may be used in place of the Hartmann plate.

Figure 10:
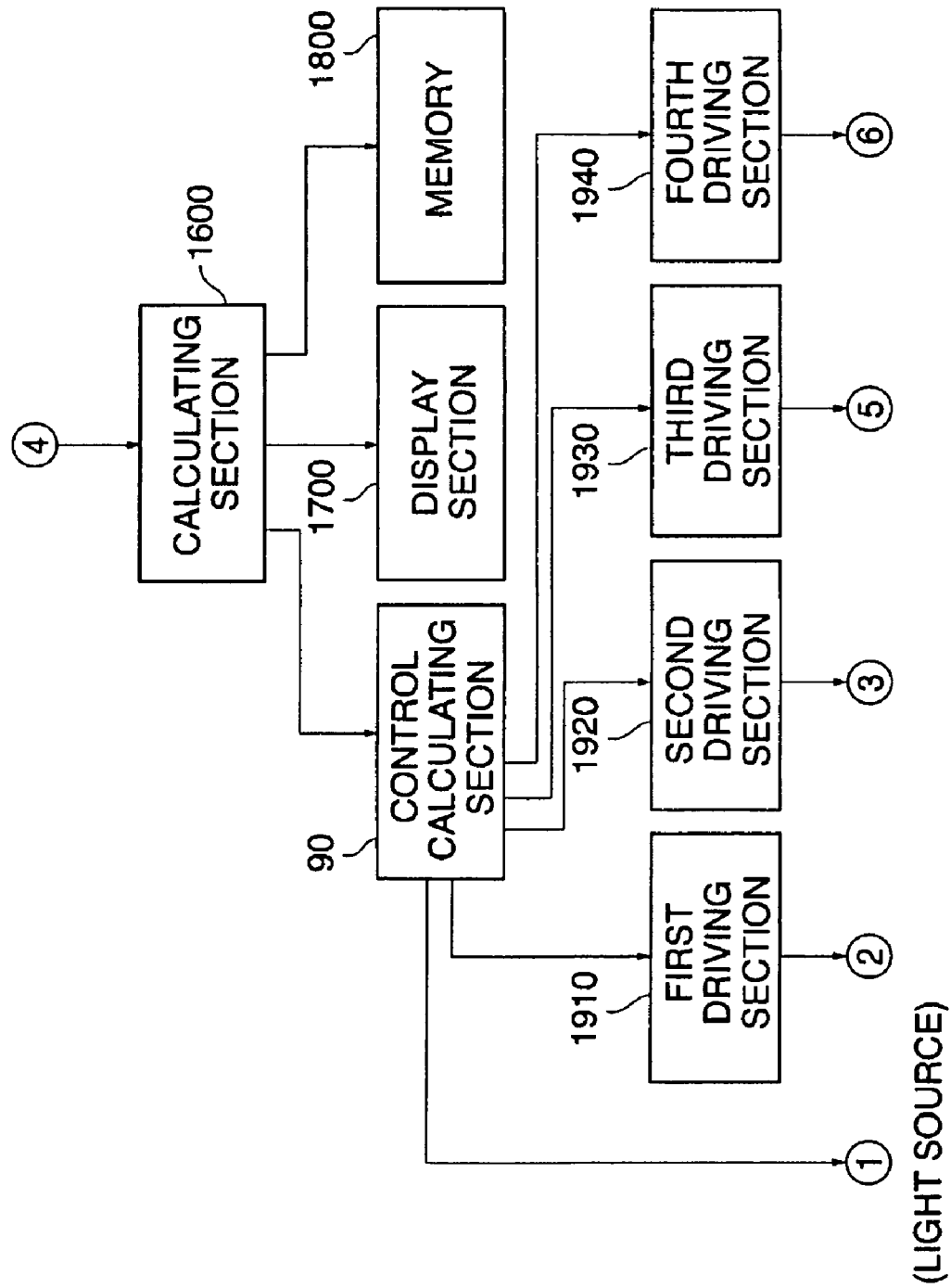
FIG. 10 shows an example of the control system for the optical characteristic measuring section.

FIG. 10 shows an example of the control system for the optical characteristic measuring section 10. Light reception output of the light receiving element 1310 is inputted to a calculating section 1600. The calculating section 1600 issues signals to a memory section 1800, a display section 1700, and the control calculating section 90. The calculating section 1600 issues a light-up driving signal to the measurement light projecting source 1260, and thereby the measurement light projecting source 1260 is lit up as required. The control calculating section 90 also controls the optical characteristic measuring section 10; It issues control drive signals to a first driving section 1910, a second driving section 1920, a third driving section 1930, and a fourth driving section 1940. The first driving section 1910 drives and rotates the variable cylinder 1280 (see FIG. 7). The second driving section 1920 drives the measuring unit 1250 (see FIG. 7) back and forth in its optical axis direction (Z direction). The third driving section 1930 drives and rotates the rotary prism 1170. The fourth driving section 1940 moves the wave-front aberration measuring section 20 and the refractive power measuring sections 50 (see FIGS. 1 and 3) as a whole in X-Y and Z directions.

The wave-front aberration measuring section 20 is to determine wave-front aberration from the optical characteristic of the subject eye E on the basis of the tilt angle of the light beam obtained with the light receiving element 1310 through the Hartmann plate 1300. The section 20 is located within the optical characteristic measuring section 10. It is made up of the Hartmann plate 1300, the light receiving element 1310, and the calculating section 1600.

The wave-front aberration is expressed with the following Zernike factors.

Z10, Z11: tilt
Z21: defocus
Z20, Z22: third-order astigmatism aberration
Z30, Z33: trefoil aberration
Z31, Z32: third-order coma aberration
Z42: third-order spherical aberration
Z41, Z43: fifth-order astigmatism aberration
Z52, Z53: fifth-order coma aberration
Z63: fifth-order spherical aberration
Z84: seventh-order spherical aberration Because the refractive power SE may be determined from the Zernike factors as described later, it may be determined using the function of the wave-front aberration measuring section 20.

In reference to FIG. 1 again, the correcting section 40 can replace lenses of glasses for the right and left subject eyes Ea and Eb. The contrast eye chart data determining section 60b determines the eye chart to be presented in the contrast eye chart presenting section 30. The contrast eye chart control section 60a controls the contrast eye chart presenting section 30 so as to present the contrast eye chart determined with the contrast eye chart data determining section 60b. The right and left subject eyes may be corrected by choosing lenses that allow them to best discern the contrast eye chart. The display section 80 displays results of measurement or analysis. The control calculating section 90 controls various sections to carry out various measurements for the subject eyes E.

FIG. 11 shows an example of process flow of the eye examination method as the first embodiment of this invention. First, refractive powers of both the subject eyes Ea and Eb of the subject in the binocular viewing state are measured with the refractive power measuring sections 50 (S10). In this embodiment, as it is possible to measure the refractive power using the optical characteristic measuring section 10, there may be cases in which the refractive power measuring sections 50 function as the optical characteristic measuring section 10. Incidentally, the refractive power SE may be determined from the following equation in which r is the pupil radius and Z is the Zernike factor.

$$SE = 4 \times Z21/r^2$$

In this way, the refractive power data and correction data for the subject eyes E in the binocular viewing state are obtained. Next in the eye chart presenting section 30, a subjective measurement eye chart to be observed by the subject is presented to the subject (S20). As the contrast eye chart, there are a combination of a pedestal eye chart and a general eyesight test chart such as the Landolt's ring eye chart and the Snellen character eye chart, and a contrast eye chart suited for measuring the space frequency characteristic (MTF: modulation transfer function) such as the Gabor stimulus.

In the apparatus constituted as described above, the eye chart presenting section 30 presents at specified timing the contrast eye chart to the front part 401 of the subject eye E for the contrast sensitivity examination. The contrast sensitivity is determined as the subject responds by telling whether or not the subject has visually recognized the contrast eye chart presented to the subject. Next, using the refractive power data of the subject eyes E, the subject eyes E in binocular viewing are corrected in the correcting section 40 (S30). In this measurement, the optimum correction data may be determined for example by repeating a process in which the refractive powers of lenses for both eyes are increased simultaneously and, when the eyesight saturates, refractive power of one of the right and left lenses is fixed and the other is changed; or, if for example correction data obtained with one eye open is available, by repeating a process in which the refractive power of one of the right and left eyes is fixed to the vicinity of that correction data and the other is changed. Incidentally, it is preferable to correct the dominant eye perfectly and to correct the other eye to become the adjusted state in the binocular viewing state. In other words, if data for the dominant eye is known when refractive power of one of the right and left lenses is left unchanged and the other is changed, changing the lens on the dominant eye side first is more efficient. Next, the optical characteristics of the subject eyes E are measured with the optical characteristic measuring section 10 as the subject observes with both eyes the subjective measurement eye chart (S40). Here, the subjective measurement eye chart is a contrast eye chart from which the optical characteristics of both eyes E in binocular viewing are obtained. Incidentally, it is also possible here to measure the wave-front aberration (S50). Next, results of measurement or analysis are displayed in the display section (S60).

Figure 12A:
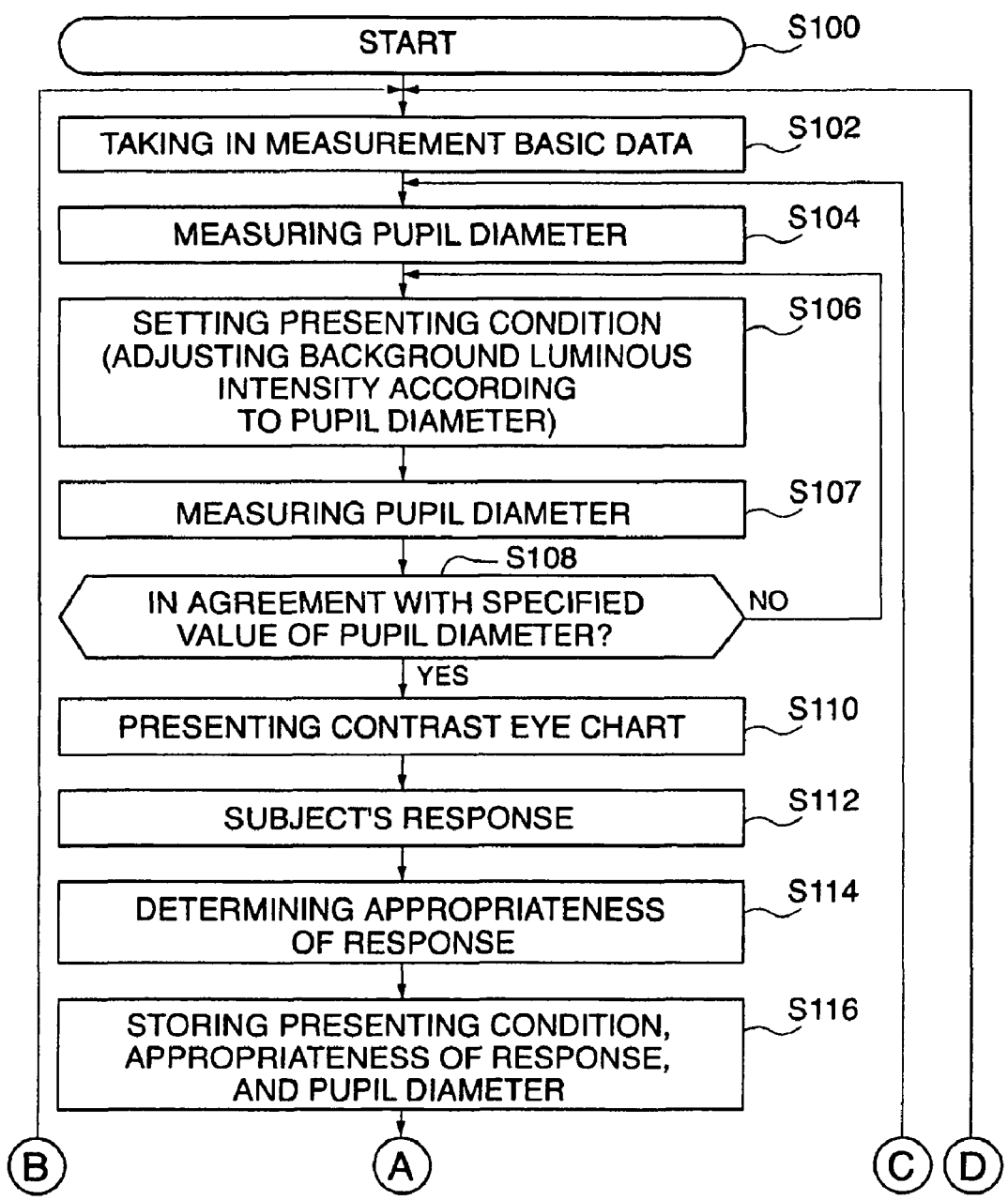
FIG. 12A is an explanatory drawing of a process flow example for contrast sensitivity measurement (first part).
Figure 12B:
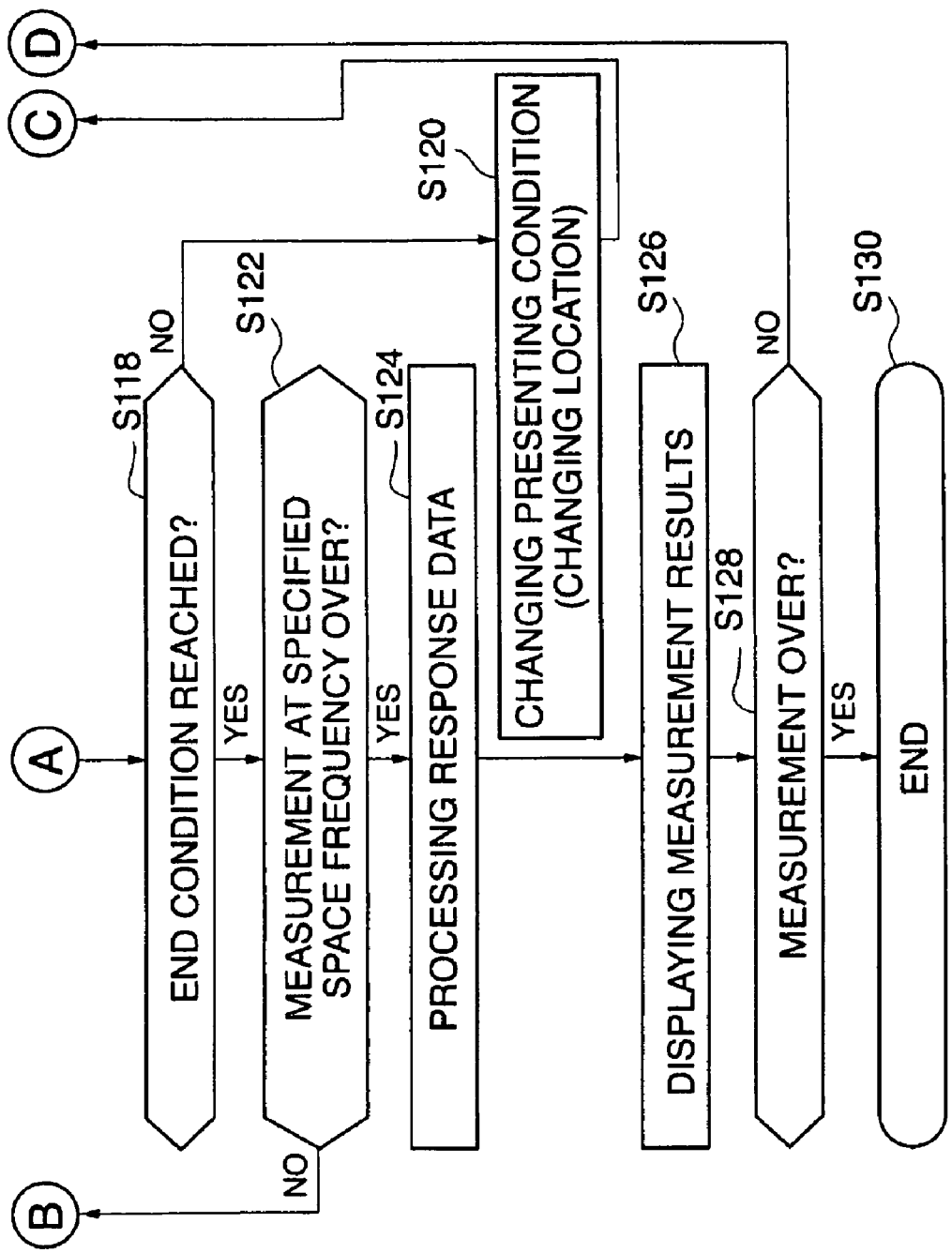
FIG. 12B is an explanatory drawing of a process flow example for contrast sensitivity measurement. (last part continuing 12A)

FIG. 12 is an explanatory drawing of a process flow example for contrast sensitivity measurement. A case is explained in which the brightness of the test eye chart is adjusted such that the pupil diameter of the subject eye E satisfies a specified value. When the measurement of the contrast sensitivity is started (S100), the contrast eye chart control section 60a takes in measurement basic data (S102). The measurement basic data includes information on the eyesight, cataract, and optic nerve disorder of the subject, and the space frequency of the contrast eye chart to be presented at this time. Next, using the observation-use CCD 2180 (see FIG. 3), an image of the front part 401 (see FIG. 4) of the subject eye E is formed and the pupil diameter of the subject eye E is measured (S104). Next, using the pedestal eye chart display control section 140 (see FIG. 4), background luminous intensity is adjusted according to the pupil diameter of the subject eye E to set the condition of presenting the test eye chart (S106). Here, the condition of presenting the test eye chart may also be set by adjusting the brightness of the test eye chart according to the pupil diameter of the subject eye E using the eye chart display control section 120 (see FIG. 4). Then, using the observation-use CCD 2180, an image of the front part 401 of the subject eye E is formed, the pupil diameter of the subject eye E is measured (S107), and a determination is made as to whether or not the pupil diameter of the subject eye E is in agreement with a specified value (S108). If not in agreement, the process goes back to the step S106. If the pupil diameter of the subject eye E is in agreement with the specified value, the contrast eye chart as a test eye chart is presented using the eye chart display control section 120 (S110).

Next, the subject responds to the contrast eye chart presented (S112). An examination technician or the contrast eye chart control section 60a (see FIG. 1) compares the subject's response with the test eye chart presented in the eye chart display control section 120 to determine whether or not the subject's response is appropriate (S114). Then, the contrast eye chart control section 60a stores: the condition of presenting the contrast eye chart, appropriateness of the response, the pupil diameter of the subject eye E, etc. (S116). Then, the examination technician or the contrast eye chart control section 60a determines if the number of test eye chart presentations has reached an end criterion, for example if the number of switching from a correct response to a wrong response, and the number of switching from a wrong response to a correct response have reached five, respectively (S118). If not reached, the condition of presenting the test eye chart is changed (S120) and the process goes back to the step S104.

If the number of presenting the test eye chart has reached the end criterion, a determination is made as to whether or not examination of the specified contrast eye chart for the space frequency is over (S122). If not over, the process goes back to the step S102 to continue the space frequency measurement. If the examination for the specified space frequency is over, the response data is processed (S124) and the measurement results are displayed (S126). Next, response history is examined to determine whether or not the space frequency of other contrast eye chart to be measured is present, and a determination is made as to whether or not the measurement is over (S128). If not over, the process goes back to the step S102 to either continue measurement of other space frequency or make examination again. If the measurement is over, the contrast sensitivity measurement for the subject is over (S130). Incidentally, an appropriate period of time for presenting the contrast eye chart at a time is clinically for example one to three seconds, preferably two seconds.

Figure 13:
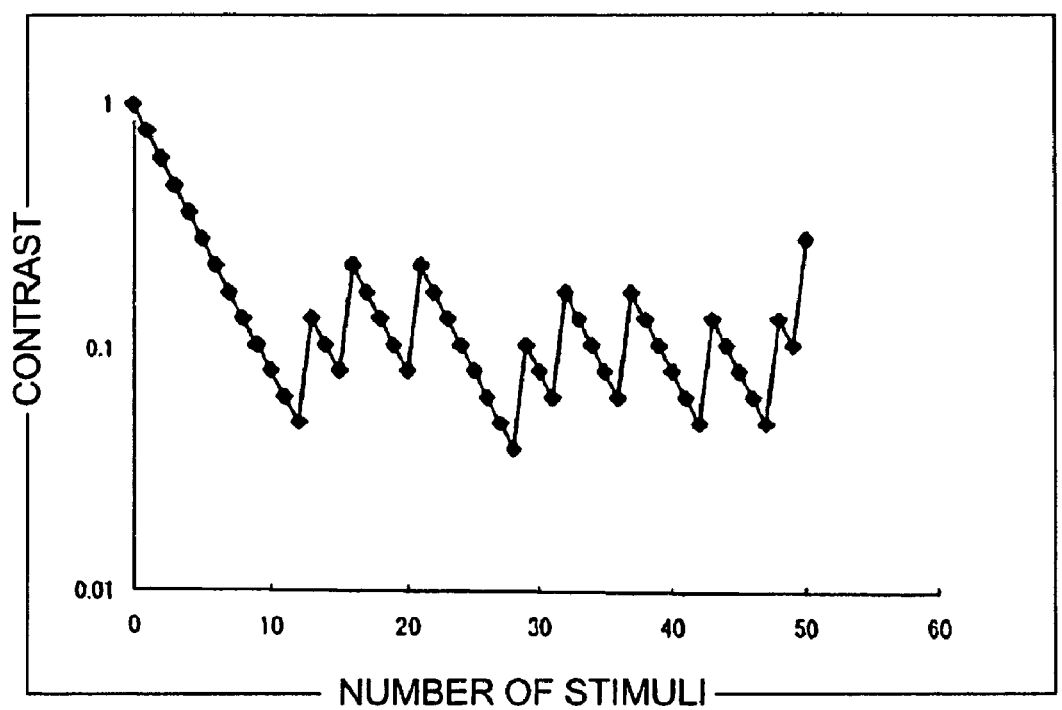
FIG. 13 shows an example of change in the contrast in the up-down method.

FIG. 13 shows an example of change in contrast in the up-down method, with the vertical axis plotting contrast, and the horizontal axis, the number of stimuli. Starting from a contrast of 100% (1 in the graph), every time the subject gives a correct response, the stimulus contrast is reduced at 0.1 logarithmic steps. When a response is incorrect, the stimulus contrast is increased by four steps. The measurement is assumed to be over when incorrect responses occur for example 5 times in decreasing directions. The contrast threshold of the subject in this case is assumed to be the average for example of 10 contrast values that have resulted in wrong responses; the threshold is for example 0.06. The contrast sensitivity is the reciprocal of the contrast threshold obtained for the subject. The average s0 and the dispersion σ of the contrast threshold may be obtained by re-arranging the results obtained in the contrast measurement using the up-down method in about five contrast levels, followed by the probit analysis, one of statistic analysis methods.

Figure 14A:
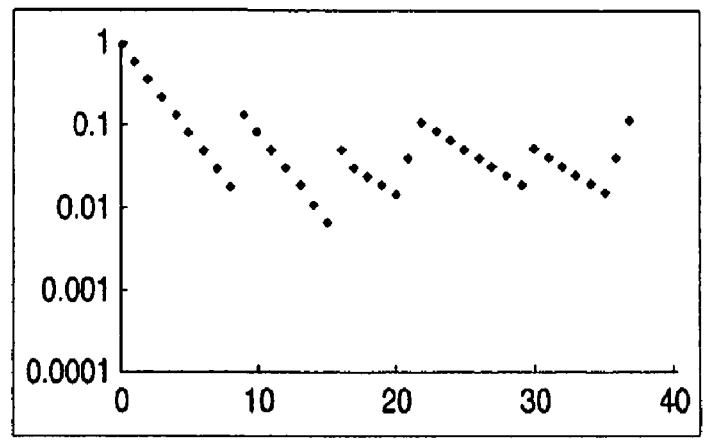
FIGS. 14A, 14B and 14C show examples of contrast sensitivity measurement results.
Figure 14B:
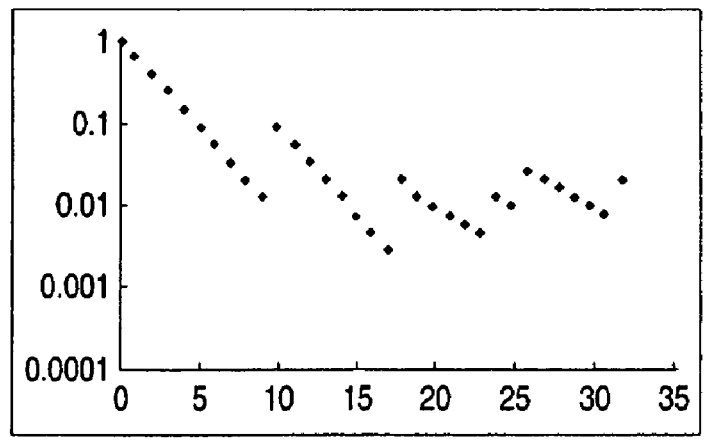
Figure 14C:
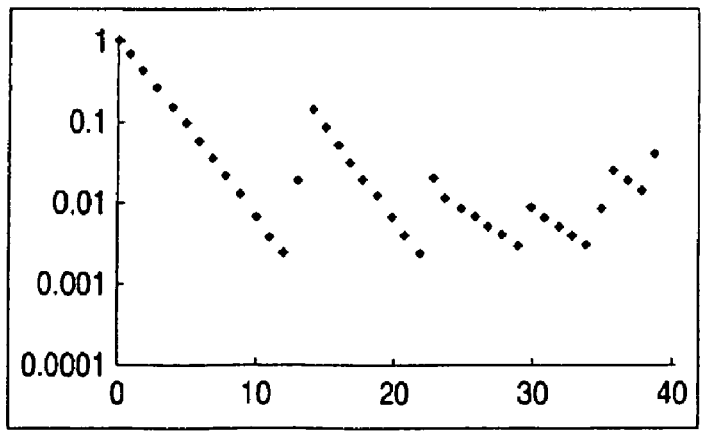

FIG. 14 shows examples of history of the subject's response to the contrast eye chart, with the vertical axis plotting the contrast, and the horizontal axis, the number of stimuli. FIG. 14A shows the response history of the right eye only; FIG. 14B, the left eye only; and FIG. 14C, both the eyes. From these figures, the contrast threshold values are known to be 0.03 for the right eye, 0.01 for the left eye, and 0.009 for both the eyes. From these figures, the sensitivity in binocular viewing is known to be superior to that in monocular viewing.

Figure 15:
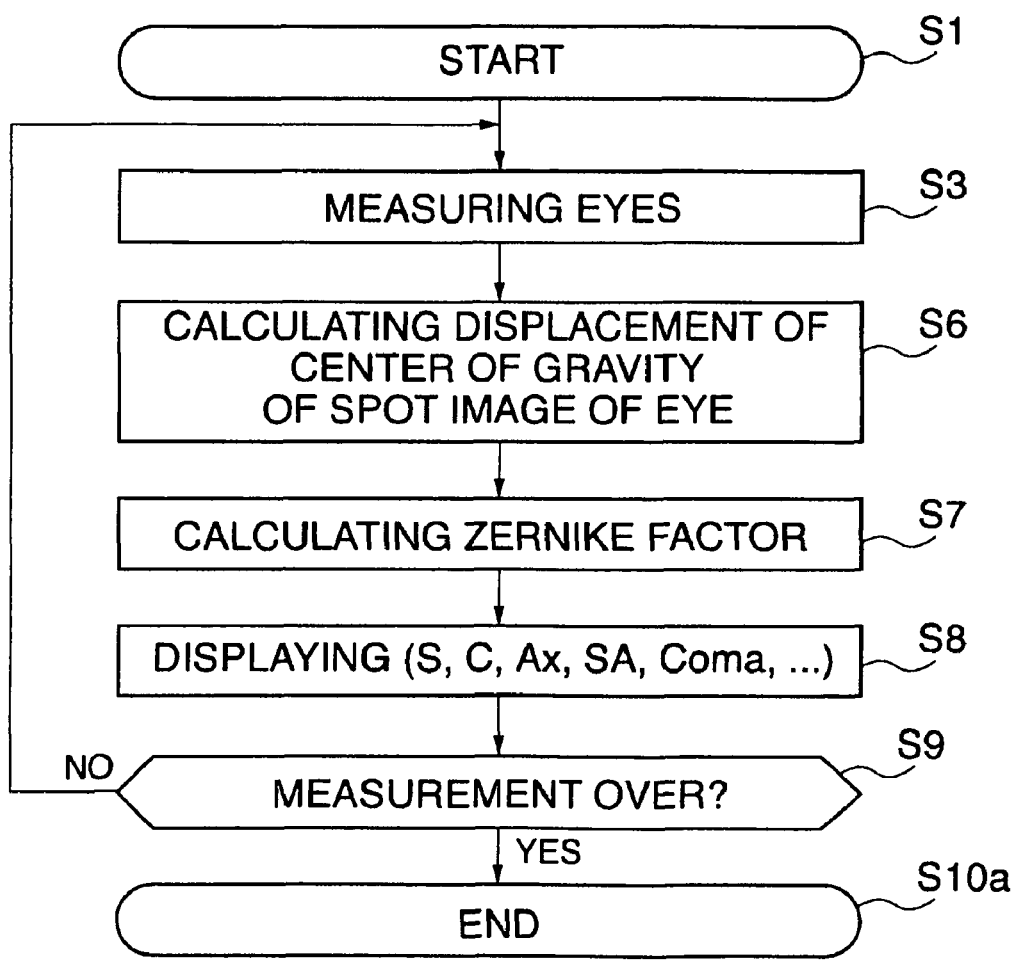
FIG. 15 shows a process flow example of the method of measuring optical characteristics.

FIG. 15 shows a process flow example of the method of measuring optical characteristics. First, in the step S1, the measurement is started.

In the step S3, "eye measurement" is made to measure the subject eye E along with aberration present in the light receiving optical system. In the step S6, the displacement amount of the center of gravity of the spot image of the subject eye E on the light receiving element 1310 (see FIG. 7) is calculated. In the step S7, Zernike factors are calculated. In the step S8, calculated values (S, C, AX, SA, Coma, . . . , etc.) are displayed on the display section 1700 (see FIG. 10). Here, the above symbols denote; S: spherical degree, C: astigmatic degree, AX: astigmatic axis angle, SA: spherical aberration, Coma: coma aberration, and . . . : high-order aberration. In the step S9, whether or not to end the measurement is determined. In the case of ending, the process goes to the step S10a to end the measurement. In the case where the measurement is not brought to an end in the step S10a, the process goes back to the step S3.

As described above, this embodiment makes it possible to provide an eye examination apparatus and an eye examination method that make it possible to measure the eyesight or contrast sensitivity in the binocular viewing state and further make it possible to measure optical characteristics in such an appropriate binocular viewing state.

Second Embodiment

This embodiment is constituted to make it possible to measure wave-front aberration in addition to optical characteristics, and to measure optical characteristics utilizing an optical characteristic section. It is also constituted to present an eye chart to a subject so as to carry out subjective measurements. In other words, the eye chart presenting section 30 (see FIGS. 1 and 3) functions as an eyesight chart presenting section that presents an eyesight chart. In place of the contrast sensitivity specifying section, an eyesight chart specifying section is used (here, it includes an eyesight chart data determining section that determines the eyesight chart and an eyesight chart control section that controls the eyesight chart presenting section so as to present the eyesight chart determined in the eyesight chart data determining section). In the refractive power measuring step S10 (see FIG. 11) and the eye chart presenting step S20 (see FIG. 11), an eye chart for measuring eyesight is used in place of the contrast eye chart used in the first embodiment. In other words, an eye chart with the Landolt's rings or the like is used. In the optical characteristic measuring step S40 (see FIG. 11), optical characteristics are measured when an eyesight chart is observed with both eyes. Optical characteristics of the subject eyes E corrected by the subjective response data of the subject are obtained. The embodiment is otherwise the same in constitution as the first embodiment.

Third Embodiment

Figure 16:
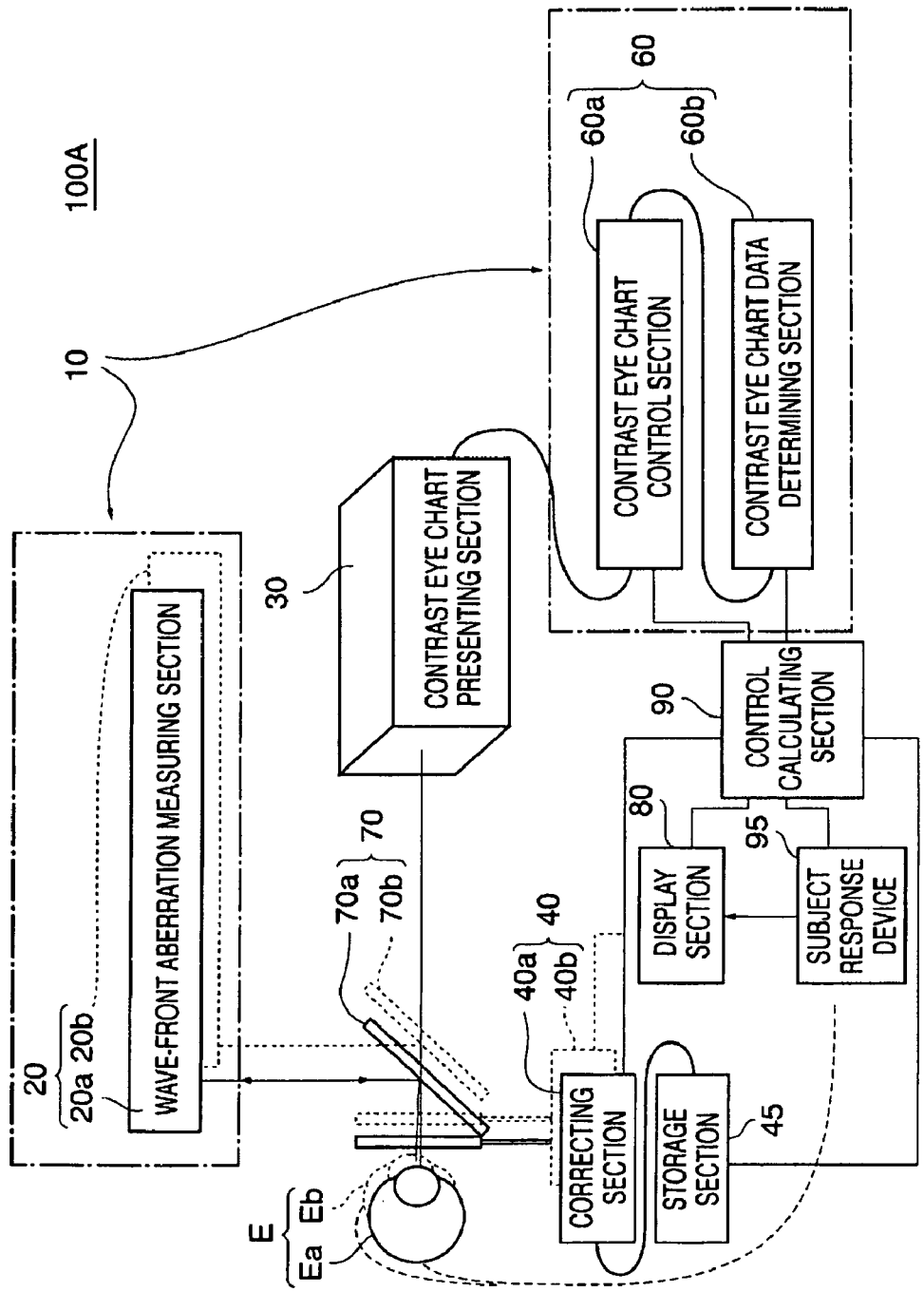
FIG. 16 shows a constitution example of the eye examination apparatus as a third embodiment of this invention.

FIG. 16 shows a constitution example of the eye examination apparatus as a third embodiment of this invention. The eye examination apparatus 100A of this embodiment is constituted without a refractive power measuring section, so that the refractive power data is obtained from other apparatuses. Here will be described only the points different from the first embodiment. As the other apparatuses, such ones may be used as a refractometer or a turret-type subjective detection apparatus (horoscope) that can measure the refractive power of the subject eye. Measurement results obtained with these apparatuses are stored in the storage section 45. The measurement results are the refractive power data of the subject eyes E in the binocular viewing state. The storage section 45 is capable of storing also the correction data and the like. The embodiment is otherwise the same in constitution as the first embodiment.

Figure 17:
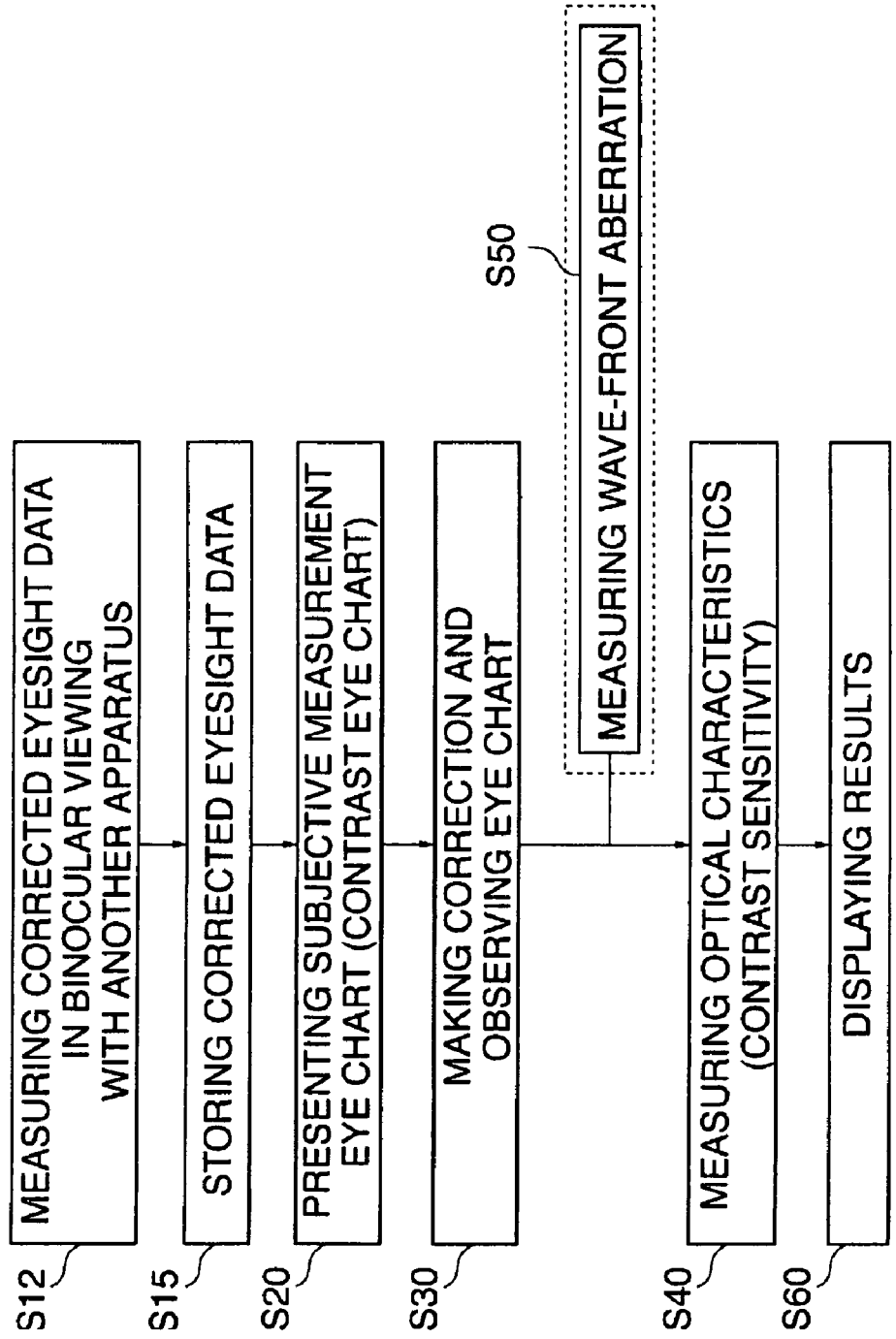
FIG. 17 shows a process flow example of the eye examination method as the third embodiment of this invention.

FIG. 17 shows a process flow example of the eye examination method as the third embodiment of this invention. First, refractive powers of both the subject eyes Ea and Eb of the subject in the binocular viewing state measured with another apparatus (S12) are acquired and stored in the storage section (S15). As a result, data on the subject's eyesight and the refractive power of the glasses for the subject are obtained. Steps thereafter are the same as those of the process flow example of the first embodiment.

Fourth Embodiment

In this embodiment, the wave-front aberration measuring section 20 may be switched between two modes, binocular viewing mode and monocular viewing mode, to measure the wave-front aberration. The wave-front aberration measuring section 20 may be switched to the first or second mode. In the first mode, the section 20 casts measurement rays simultaneously to both the subject eyes E so as to converge the rays at a point on the fundi of the subject eyes E and receives rays reflected from the subject eyes E to measure the wave-front aberration. In the second mode, the section 20 casts measurement rays to one subject eye E at a time to objectively measure the refractive power so as to converge the rays at a point on the fundus of the subject eye E and receives the rays reflected from the subject eye E to measure the wave-front aberration. The switching may be made for example by replacing the lens with a blind plate in the correcting section 40. In this way, it is possible to measure the wave-front aberration in both the binocular and monocular viewing states and it is also possible to compare the data between both the viewing states.

Fifth Embodiment

Figure 18:
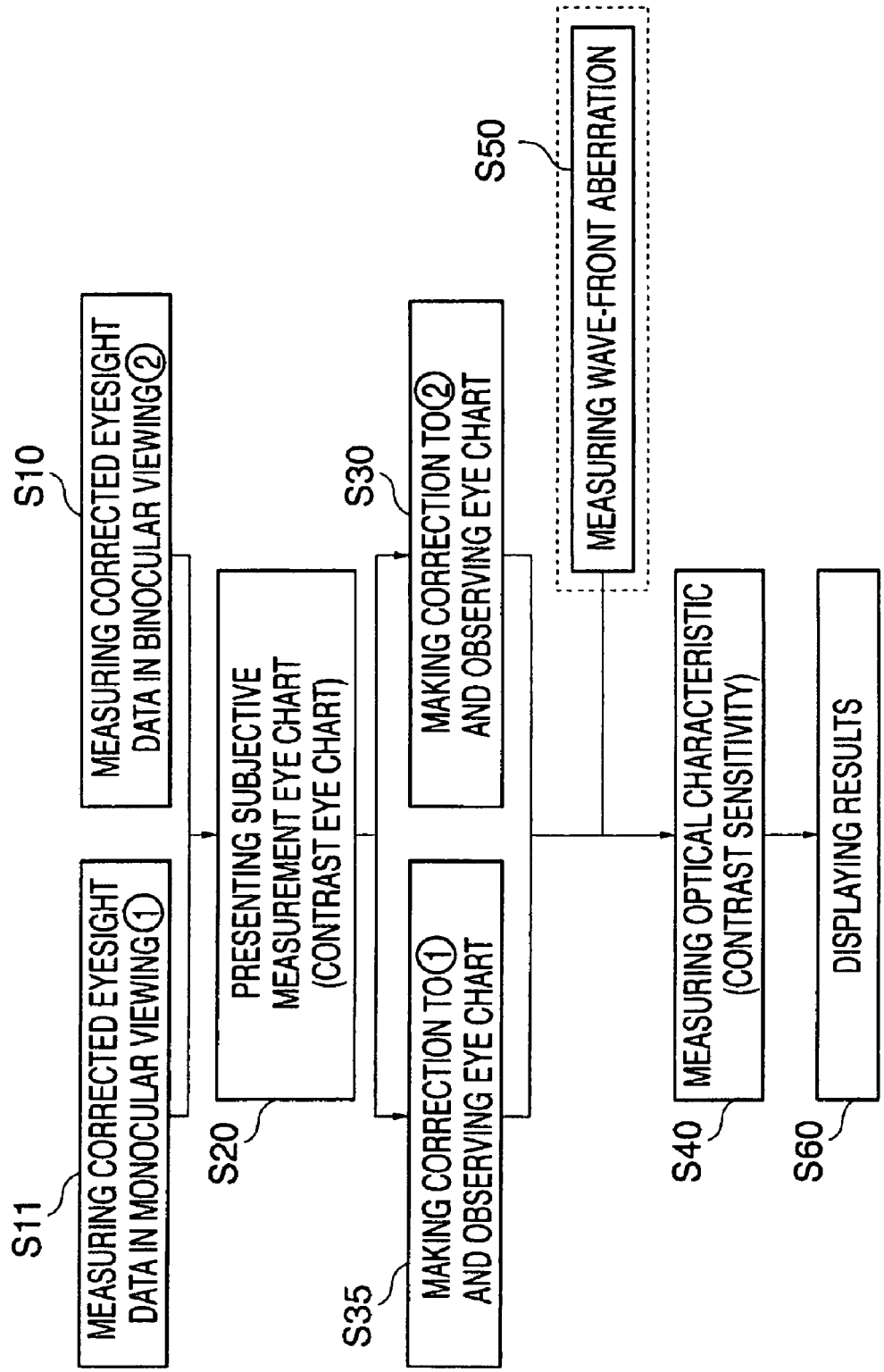
FIG. 18 shows a process flow example of the eye examination method as a fifth embodiment of this invention.

FIG. 18 shows a process flow example of the eye examination method as a fifth embodiment of this invention. While the description of the above embodiments is centered on binocular viewing, this embodiment is an example capable of measurement with monocular viewing in addition to measurement with binocular viewing. The apparatus constitution is similar to that of the first embodiment, except a blind plate for blocking the field of vision on one eye is placed in the correcting section 40. First, the refractive power measuring section 50 measures the refractive power of both the subject eyes E of the subject in the monocular or binocular viewing state (S10 or S11). Next with the eye chart presenting section 30, a subjective measurement eye chart is presented to be observed by the subject (S20). Next, using the refractive power data of the subject, the subject eyes E in the binocular viewing state are corrected using the correcting section 40 (S30 or S35). Refractive power data in binocular viewing is used for correction in binocular viewing; and refractive power data in monocular viewing is used for correction in monocular viewing. Next with the optical characteristic measuring section 10, optical characteristics of the subject are measured while the subject is observing a subjective measurement eye chart in the binocular or monocular viewing state (S40). Incidentally, it is also possible here to measure the wave-front aberration (S50). Next, results of measurement or analysis are displayed (S60). In this way, this embodiment makes it possible to make measurements in monocular viewing as well as in binocular viewing.

Sixth Embodiment

FIG. 19 shows a process flow example of the eye examination method as a sixth embodiment of this invention. First, refractive powers of both the subject eyes E of the subject in the binocular or monocular viewing state measured with another apparatus (S11 or S12) are acquired and stored in the storage section (S15). Thus, data on the subject's eyesight and the refractive power of the glasses for the subject are obtained. Steps thereafter are the same as those of the process flow example of the fifth embodiment.

Also with the second through the sixth embodiment, it is possible to provide an eye examination apparatus and an eye examination method capable of measuring eyesight or contrast sensitivity in the binocular viewing state, and further capable of measuring optical characteristics in such an appropriate binocular viewing state.

Further, this invention may also be realized as a program for causing a computer to implement the eye examination method described in the above embodiments. The program may be stored in a built-in memory in the control section for use, stored in a memory device inside or outside the eye examination apparatus for use, or downloaded from the Internet for use. It may also be realized as a storage medium storing such a program.

While the embodiments of this invention are described above, this invention is not limited to the above embodiments. Rather, it is apparent that this invention may be subjected to various modifications without departing from the spirit of this invention.

For example, while a mode of embodiment capable of measuring the wave-front aberration is described above, it is also acceptable if the wave-front aberration cannot be measured. Further, while a mode is described in which the refractive power and the wave-front aberration can be measured mainly with the optical characteristic measuring section, a refractive power measuring section and a wave-front aberration measuring section may be provided independently to measure refractive power and wave-front aberration. While the second embodiment is described as an example in which the same optical system is used by replacing the eyesight chart with the contrast eye chart, it is also possible to use respectively independent optical systems by changing over one from to another. Further, while the third embodiment is described as an example that does not include a refractive power measuring section and acquires the refractive power data from other apparatus, it may also be one that includes a refractive power measuring section but acquires the refractive power data from another apparatus. Further, while the measurements in the binocular and monocular viewing states are described separately in the above embodiments, it is also possible to make the binocular and monocular viewing states switchable to carry out measurements by appropriately switching between both the states, or carry out correction or measurement of optical characteristics while comparing data between both the states. For example, it is possible to correct binocular viewing using refractive power data in monocular viewing, or correct monocular viewing using refractive power data in binocular viewing. Further in the contrast sensitivity measurement, luminance of the pupil diameter measurement light path may be measured and adjusted, or the pupil diameter may not be measured. Further in the optical characteristic measuring section, spot image may be adjusted using an alignment optical system, or may not be adjusted. Moreover, it is possible to variously change layout of optical devices and details of eye charts and contrast eye charts.

The present invention may be utilized in eye examination in the binocular viewing state.

DESCRIPTION OF REFERENCE NUMERALS AND SYMBOLS

10: optical characteristic measuring section
20: wave-front aberration measuring section
30: contrast eye chart presenting section
40: correcting section 45: storage section
50: refractive power measuring section
60: contrast sensitivity specifying section
70: dichroic mirror
80: display section
90: control calculating section
100, 100A: eye examination apparatus
110: first illumination optical system
111: light source
112: condenser lens
113: rotary motor for replacing eye charts
114: eye chart plate
115: ND filter
116: magnification correcting lens
117: diffusion plate
120: test eye chart display control section (eye chart brightness control means)
125: eye chart brightness adjusting section
130: second illumination optical system
131: light source
132: condenser lens
133: rotary motor for replacing eye charts
134: eye chart plate
135: ND filter
136: magnification correcting lens
137: diffusion plate
140: pedestal eye chart display control section (background illumination control means)
145: background illumination adjusting section
151: mirror
95: subject response device
300: contrast eye chart presenting system
400: subject eye
401: front part of the eye
402: crystalline lens
1260: measurement light source
1270: light receiving optical system
1280: variable cylinder
1290: condenser lens
1300: Hartmann plate
1310: light receiving element
1600: calculating section
1610: control section
1700: display section
1800: memory
1910: first driving section
1920: second driving section
1930: third driving section
1940: fourth driving section
2100: light source
2110: pinhole
2120: condenser lens
2130: half-reflecting mirror
2140: dichroic mirror
2150: condenser lens
2160: spotlight source
2170: ring-shaped light source
2180: observation-use CCD
2190: motor
2200: computer
B: stage
E, Ea, Eb: subject eye

What is claimed is:

1. An eye examination apparatus comprising:
a refractive power measuring section for objectively measuring refractive powers of subject eyes of a subject in a binocular viewing state;
an eye chart presenting section for presenting a subjective measurement eye chart to be observed by the subject;
a correcting section for correcting the subject eyes by referring to data on the refractive powers measured with the refractive power measuring section and using the subjective measurement eye chart presented in the eye chart presenting section; and
an optical characteristic measuring section for subjectively measuring an optical characteristic of each of the subject eyes corrected or being corrected with the correcting section in a state where the subject is binocularly viewing the subjective measurement eye chart,
wherein the subjective measurement eye chart is an eye chart for subjectively measuring contrast sensitivity, and the optical characteristic measuring section is constituted to subjectively measure the contrast sensitivity of the subject.

2. The eye examination apparatus as recited in claim 1, comprising a wave-front aberration measuring section for measuring the wave-front aberration of the subject eyes in the state where the subject is binocularly viewing the subjective measurement eye chart, based on a light reception signal occurring when a light receiving element receives light which is cast as measurement-use light so as to converge at a point on a fundus of the subject eye and is reflected from the fundus of the subject eye.

3. An eye examination apparatus comprising:
a refractive power measuring section for objectively measuring refractive powers of subject eyes of a subject in a binocular viewing state;
an eye chart presenting section for presenting a subjective measurement eye chart to be observed by the subject;
a correcting section for correcting the subject eyes by referring to data on the refractive powers measured with the refractive power measuring section and using the subjective measurement eye chart presented in the eye chart presenting section;
an optical characteristic measuring section for subjectively measuring an optical characteristic of each of the subject eyes corrected or being corrected with the correcting section in a state where the subject is binocularly viewing the subjective measurement eye chart; and
a wave-front aberration measuring section for measuring the wave-front aberration of the subject eyes in the state where the subject is binocularly viewing the subjective measurement eye chart, based on a light reception signal occurring when a light receiving element receives light which is cast as measurement-use light so as to converge at a point on a fundus of the subject eye and is reflected from the fundus of the subject eye,
wherein the wave-front aberration measuring section has:
a first mode in which measurement-use light is cast to enter both the subject eyes at the same time so as to converge at a point on the fundi, and the lights reflected from the subject eyes are received to measure the wave-front aberration of the subject eyes; and
a second mode in which, in order to objectively measure the refractive power, measurement-use light is cast to enter the subject eyes one by one so as to converge at a point on the fundus, and the light reflected from the subject eye is received to measure the wave-front aberration of the subject eye.

4. The eye examination apparatus as recited in claim 2, wherein the wave-front aberration measuring section has:
a first mode in which measurement-use light is cast to enter both the subject eyes at the same time so as to converge at a point on the fundi, and the lights reflected from the subject eyes are received to measure the wave-front aberration of the subject eyes; and a second mode in which, in order to objectively measure the refractive powers, measurement-use light is cast to enter the subject eyes one by one so as to converge at a point on the fundus, and the light reflected from the subject eye is received to measure the wave-front aberration of the subject eye.

5. An eye examination method, comprising:

a refractive power measuring step of objectively measuring refractive powers of subject eyes of a subject in a binocular viewing state;

an eye chart presenting step of presenting a subjective measurement eye chart to be observed by the subject;

a correcting step of correcting the subject eyes by referring to data of the refractive powers measured in the refractive power measuring step and using the subjective measurement eye chart presented in the eye chart presenting step; and an optical characteristic measuring step of subjectively measuring an optical characteristic of each of the subject eyes corrected or being corrected in the correcting step in a state where the subject is binocularly viewing the subjective measurement eye chart, wherein the subject eyes are corrected in the correcting step such that when contrast sensitivity or eyesight is measured, a dominant eye is corrected perfectly and the other eye is corrected so as to be adjusted in the binocular viewing state.

6. The eye examination apparatus as recited in claim 1, further comprising a wave-front aberration measuring section for measuring a wave-front aberration of the subject eyes.

* * * * *